(12) United States Patent
Zanon et al.

(10) Patent No.: US 12,133,726 B2
(45) Date of Patent: Nov. 5, 2024

(54) DETECTION OF GAIT ACTIVITY

(71) Applicant: Hoffmann-La Roche Inc., Little Falls, NJ (US)

(72) Inventors: Mattia Zanon, Zurich (CH); Lorenza Angelini, Riehen (CH); Dimitar Yuriev Stanev, Basel (CH)

(*) Notice: Subject to any disclaimer, the term of this patent is extended or adjusted under 35 U.S.C. 154(b) by 0 days.

(21) Appl. No.: 18/411,567

(22) Filed: Jan. 12, 2024

(65) Prior Publication Data

US 2024/0268709 A1 Aug. 15, 2024

(30) Foreign Application Priority Data

Feb. 14, 2023 (EP) .................................... 23156442

(51) Int. Cl.
*A61B 5/11* (2006.01)
*A61B 5/00* (2006.01)

(52) U.S. Cl.
CPC ............ *A61B 5/112* (2013.01); *A61B 5/4076* (2013.01); *A61B 5/4842* (2013.01); *A61B 5/4848* (2013.01); *A61B 5/6802* (2013.01); *A61B 5/725* (2013.01); *A61B 5/726* (2013.01); *A61B 2562/0219* (2013.01)

(58) Field of Classification Search
CPC ..... A61B 5/112; A61B 5/4076; A61B 5/4842; A61B 5/4848; A61B 5/6802; A61B 5/725; A61B 5/726; A61B 2562/0219
See application file for complete search history.

(56) References Cited

U.S. PATENT DOCUMENTS

| | | | | |
|---|---|---|---|---|
| 2021/0315488 A1* | 10/2021 | McDaid | ................. | A61H 1/024 |
| 2021/0389159 A1* | 12/2021 | Kelly | ..................... | G01C 21/14 |
| 2023/0123815 A1* | 4/2023 | Suárez | ................... | G06V 40/20 |
| | | | | 600/301 |

OTHER PUBLICATIONS

Tietsch, Matthias et al. "Robust Step Detection from Different Waist-Worn Sensor Positions: Implications for Clinical Studies" Nov. 26, 2020. Digit Biomark. 2020 Winter; 4 (Suppl 1): 50-58. Retrieved from Karger. (Year: 2020).*
Tietsch, Matthias et al. "Supplementary Materials: Robust Step Detection from Different Waist-Worn Sensor Positions: Implications for Clinical Studies" Nov. 26, 2020. Digit Biomark. 2020 Winter; 4 (Suppl 1): 1-5. Retrieved from Karger. (Year: 2020).*

(Continued)

*Primary Examiner* — May A Abouelela
*Assistant Examiner* — Anna Roberts
(74) *Attorney, Agent, or Firm* — Jones Day

(57) ABSTRACT

The present disclosure relates to systems and methods for processing signals from wearable motion sensors associated with gait activity of a subject. In some cases, a signal representative of the gait activity of the subject may be received from the wearable motion sensors. One or more directional components of the signal, which are independent of an orientation of the wearable motion sensors on the subject, may be identified. One or more gait features may be extracted from the signal based on the one or more directional components of the signal. At least one of a diagnosis, a progression, a treatment, and a treatment response for a neurological dysfunction may be determined based on the one or more gait features.

19 Claims, 14 Drawing Sheets

(56) References Cited

OTHER PUBLICATIONS

Angelini, Lorenza, et al. "A Multifactorial Model of Multiple Sclerosis Gait and Its Changes Across Different Disability Levels" Feb. 24, 2021. IEEE. vol. 68, Iss. 11. Retrieved from IEEE. (Year: 2021).*

Escamilla-Nunez, Rafael et al."Derivative Based Gait Event Detection Algorithm Using Unfiltered Accelerometer Signals" Jul. 2020. Annu Int Conf IEEE Eng Med Biol. Soc. 4487-4490. (Year: 2020).*

* cited by examiner

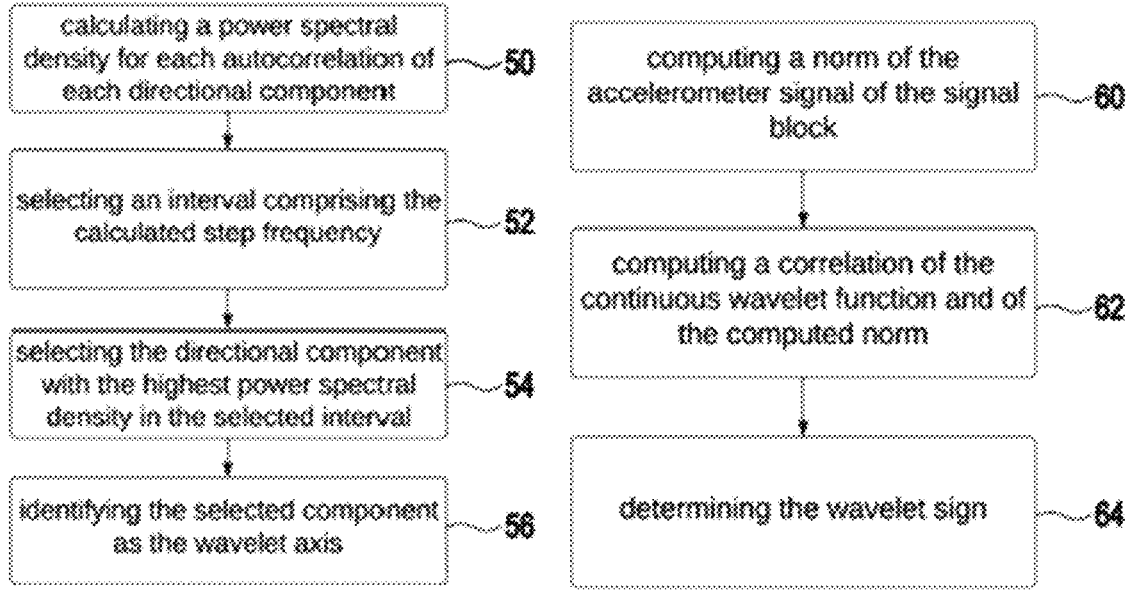
Fig. 5
Fig. 6
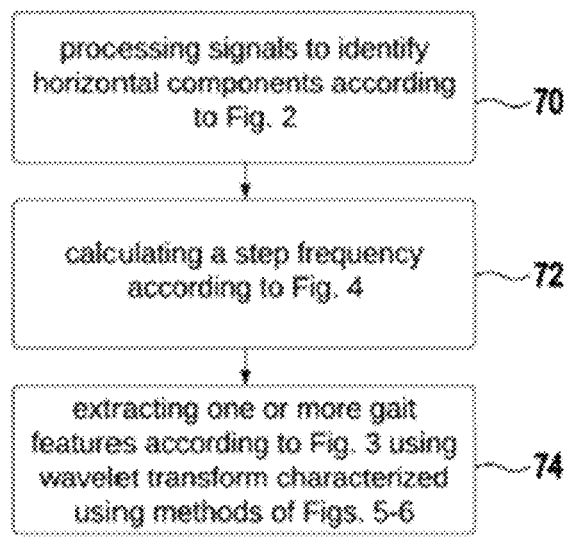
Fig. 7

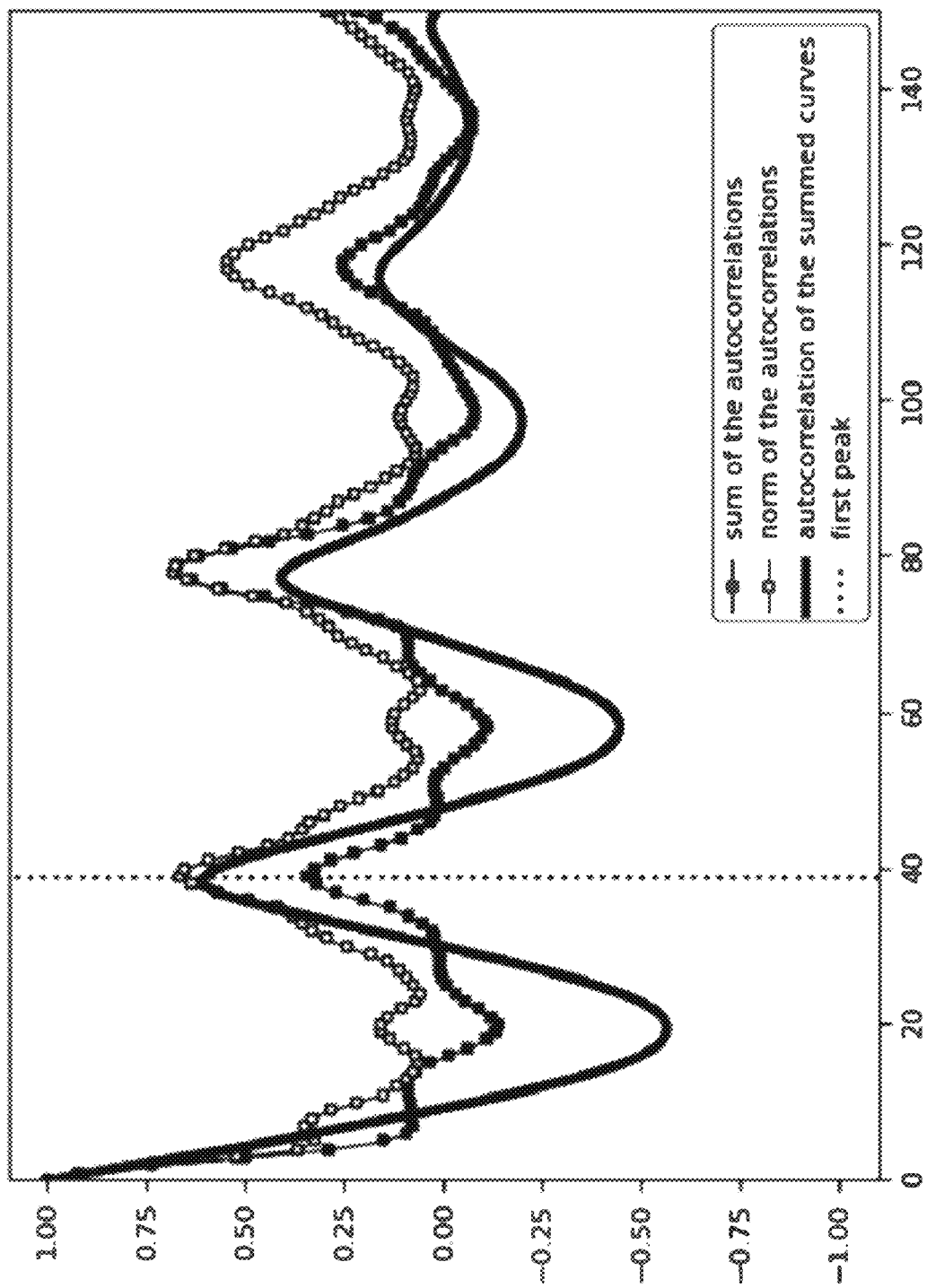

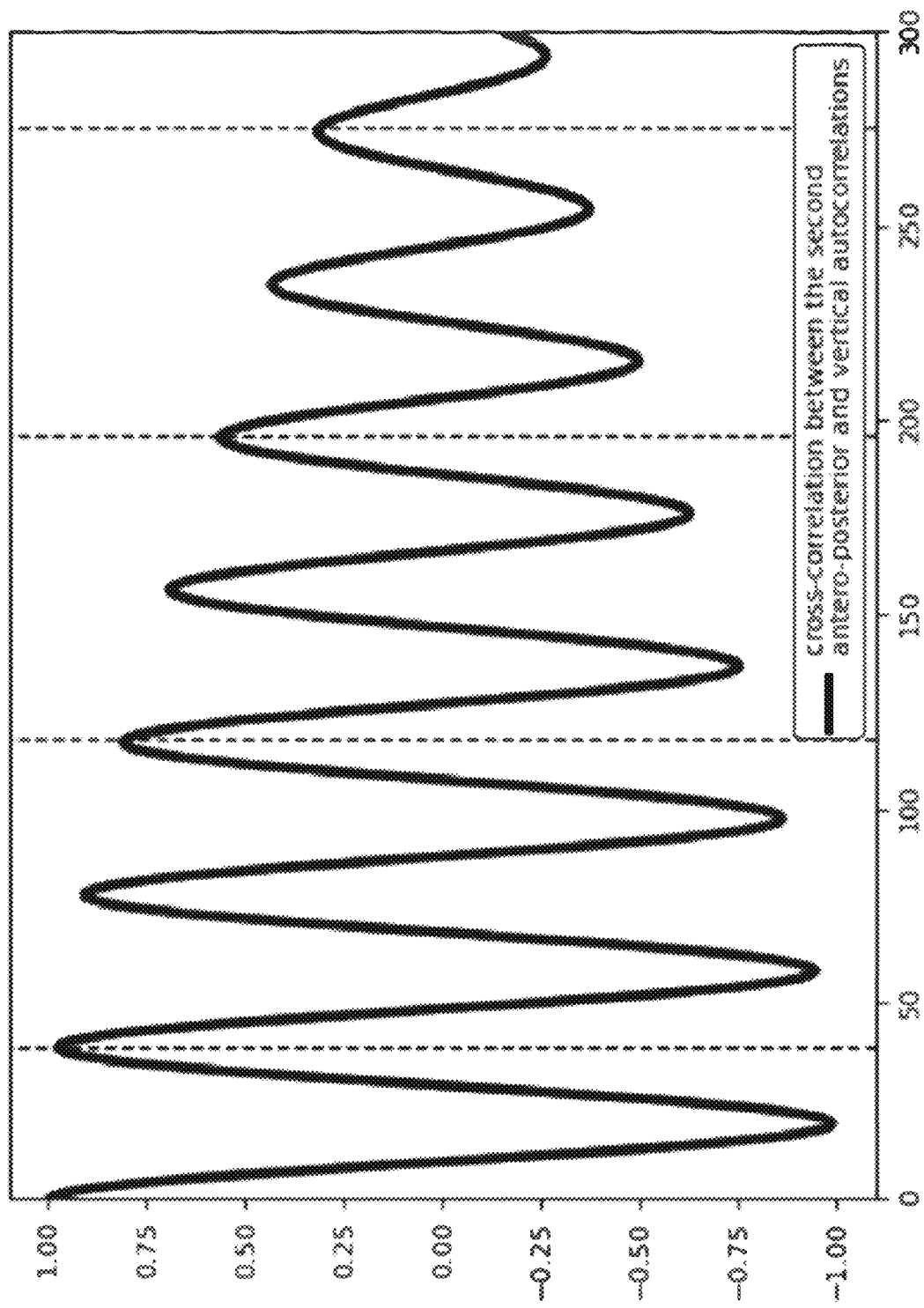

DETECTION OF GAIT ACTIVITY

CROSS REFERENCE TO RELATED APPLICATION

This application claims priority to European Application No. 23156442.8, entitled "DETECTION OF GAIT ACTIVITY" and filed on Feb. 14, 2023, the disclosure of which is incorporated herein by reference in its entirety.

TECHNICAL FIELD

The present disclosure relates to systems and methods for processing signals from wearable motion sensors associated with gait activity of a subject.

INTRODUCTION

Neurological diseases such as multiple sclerosis (MS), Parkinson's disease, Huntington's disease, often manifest themselves with symptoms like impaired posture and gait. These impairments are used as clinical indications of the disease progression. Precise assessments of gait abnormalities are particularly important to detect early-stage dysfunctions.

The use of technological devices such as wearable motion sensors at the ankles or in the lumbar region has greatly simplified gait detection and monitoring. The gyroscope and the accelerometer embedded in those sensors allow for measuring respectively the rotational changes and the linear changes relative to the frame of reference of the device. Methods exist that analyze gyroscope and accelerometer data to identify specific gait features of a subject, e.g. the characteristic motor patterns preceding the freezing of gait, e.g., the brief, episodic absence or marked reduction of forward progression typical of Parkinson's disease (Palmerini et al, 2017). However, while such methods can discriminate between rest and gait patterns, they have a number of limitations and fail to detect more granular gait features defining real-life gait activity.

However, these methods rely on the assumed location and/or orientation of the sensors on the subject to define the sensors' frame of reference. Any misplacement or misalignment of the sensors can result in inaccurate or wrong analysis results. Moreover, sensors placed at the same location on different subjects can have a different orientation depending on, for example, the subjects' body shape. Consequently, it is impossible to compare the gait features obtained with such methods among different subjects and/or sensors locations, in clinical settings as well as in unsupervised environments. Moreover, while state-of-the-art methods can discriminate between rest and general types of gait patterns such as normal and pathological gait, they fail to detect more granular gait features of clinical relevance.

Therefore there is a need for improved systems and methods for processing signals from wearable motion sensors associated with gait activity of a subject.

SUMMARY

The present disclosure relates to systems and methods for processing signals from wearable motion sensors associated with gait activity of a subject. The methods may find particular use in the analysis of gait activity of a subject with a neurological dysfunction, such as Multiple Sclerosis (MS). These methods can be used, among other applications, to monitor disease progression, to assess the response of patients to a treatment in clinical studies, to compare the performance of a subject at a plurality of time points or the performance of different subjects in supervised or unsupervised environments.

Conventional approaches for gait analysis are problematic because they rely on the assumed location and/or orientation of the sensors on the subject to define the sensors' frame of reference. Any misplacement or misalignment of the sensors can result in inaccurate or wrong analysis results. Moreover, sensors placed at the same location on different subjects can have a different orientation depending on, for example, the subjects' body shape. Consequently, it is impossible to compare the gait features obtained with such methods among different subjects and/or sensors locations, in clinical settings as well as in unsupervised environments.

Various implementations of the subject matter disclosed herein obviate the aforementioned limitations of conventional gait analysis methodologies by at least leveraging specific operations on the signals received from wearable motion sensors including, for example autocorrelations, sums, norms, and/or the like. Doing so correctly decomposes the signals in the triad of orthogonal components in the global walking directions including, for example, the vertical component along the direction of gravity, the antero-posterior component along the direction of walking, the medio-lateral component, and/or the like. Processing the signals with the computer-implemented method of the present disclosure to identify said directional components thus allows gait activity of a subject to be analyzed independently of the position and/or orientation of the sensors on the subject. Furthermore, in some example embodiments disclosed herein, parts of the signals (e.g., signal blocks) may be classified into categories based on the type of motion thereby encoded, which allows for a more accurate identification of clinically relevant gait features. For example, by selecting signal blocks categorized as straight-gait blocks, it is possible to accurately infer, from the signal components along the global walking directions, a variety of gait features such as step duration, stride duration, step frequency, and/or the like.

Thus, according to a first aspect, the present disclosure provides a computer-implemented method of processing signals from one or more wearable motion sensors to analyze gait activity of a subject, the method comprising: receiving signals from the one or more wearable motion sensors located in any orientation on the subject, wherein the one or more wearable motion sensors comprise an accelerometer and a gyroscope; and processing the received signals, wherein processing comprises: dividing the signals from each sensor into a plurality of signal blocks comprising the signal of the respective sensor over a time interval; determining, for at least one of the plurality of signal blocks, directional components of the signal block, wherein determining directional components comprises: determining a vertical component of the signal block along the direction of gravity; estimating horizontal components of the signal block in the plane perpendicular to the direction of gravity, wherein the horizontal components includes an antero-posterior component and a medio-lateral component; computing a vertical autocorrelation of the vertical component of the signal block; computing a horizontal autocorrelation of each estimated horizontal component of the signal block; calculating an autocorrelation sum of the horizontal autocorrelations of each horizontal component and of the vertical autocorrelation of the vertical component; calculating an autocorrelation norm of the horizontal autocorrelations of each horizontal component and of the vertical autocorrelation of the vertical component; calculating a sum of the autocorrelation sum of autocorrelations and of the autocorrelation norm of autocorrelations; computing an autocorrelation of the sum; estimating the location of the first peak of the autocorrelation; selecting, in each horizontal autocorrelation of the horizontal components, the peak located at the location of the first peak; validating the horizontal components of the signal blocks using one or more predetermined criteria that apply to the signs of the selected peaks of each horizontal autocorrelation of the horizontal components.

The calculating of the autocorrelation sum of the horizontal autocorrelations of each horizontal component and of the vertical autocorrelation of the vertical component can be performed using Equation 1.

The calculating of the autocorrelation norm of the horizontal autocorrelations of each horizontal component and of the vertical autocorrelation of the vertical component can be performed using Equation 2.

The calculating of the sum of the autocorrelation sum of autocorrelations and of the autocorrelation norm of autocorrelations can be performed using Equation 3.

The validating of the horizontal components of the signal block using one or more predetermined criteria that apply to the signs of the selected peaks of each horizontal autocorrelation of the horizontal components can comprise: determining, based on the results of evaluation of the one or more predetermined criteria, that the estimated horizontal components are correctly identified, and/or determining, based on the results of evaluation of the one or more predetermined criteria, that the estimated horizontal components are incorrectly identified. The said criteria are based on the biphasic nature of the antero-posterior component of a signal associated with gait activity and of the monophasic nature of the medio-lateral component of a signal associated with gait activity. In particular, the estimated horizontal components are correctly identified when: the selected peak of the antero-posterior component is positive and the selected peak of the medio-lateral component is negative; or the selected peak of the antero-posterior component and the selected peak of the medio-lateral component are negative and the selected peak of the antero-posterior component is the highest in absolute value. In particular, the estimated horizontal components are incorrectly identified when: the selected peak of the antero-posterior component is negative and the selected peak of the medio-lateral component is positive; or the selected peak of the antero-posterior component and the selected peak of the medio-lateral component are negative and the selected peak of the medio-lateral component is the highest in absolute value. In other words, the autocorrelation of the biphasic antero-posterior component should show a first positive peak while the autocorrelation of the monophasic medio-lateral component should show a first negative peak. If both first peaks are negative, the antero-posterior component should be selected as the component with the highest absolute value, given that the main direction of motion is the antero-posterior (e.g., forward/backward).

The determining that the estimated horizontal components are incorrectly identified can comprise identifying correctly the estimated horizontal components. In particular, the estimated antero-posterior component incorrectly identified corresponds to the correctly identified medio-lateral component and the estimated medio-lateral component incorrectly identified corresponds to the correctly identified antero-posterior component. In other words, once the horizontal components are incorrectly identified, they are swapped to be correctly identified.

The computed autocorrelations of the directional components contain information about the gait activity. In particular, the location of the first peak of the autocorrelations (positive for the vertical component and for the antero-posterior component, and negative for the medio-lateral component) quantifies the step duration. Similarly, the location of the second peak of the horizontal autocorrelations and vertical autocorrelation (positive for all three components) quantifies the stride duration. In the literature, a step frequency is estimated directly using the information of the peaks of such autocorrelations. However, the computed autocorrelations of the directional components can contain noise and/or spurious peaks, thus prejudicing the correct estimation of step duration and stride duration. Computing the autocorrelation sum and the autocorrelation norm of the autocorrelations of the directional components and autocorrelating their sum allows for noise removal and spurious peak rejection, thus improving the quantification of said gait features. Additionally, the location of the first peak of the autocorrelation of their sum can be used as a benchmark for validating the estimated directional components as hereinbefore described.

The method can have one or more of the following features.

Signals are received from one or more wearable sensors located in any orientation on the subject including by at least one of receiving signals directly from one or more sensors, and/or receiving signals previously acquired by one or more sensors, from a user (e.g. through a user interface), from a computer, from a transmitting device, or from a data store. the receiving of signals from one or more wearable sensors located in any orientation on the subject can comprise receiving signals previously obtained during one or more tests performed by the subject. The one or more tests can comprise active tests and/or passive tests. An active test can be selected from a 2MWT (2-Minute-Walking-Test), a U-Turn Test, and a SBT (Static Balance Test). A passive test can be passive monitoring. The subject can be a human subject. The subject can be an adult subject. The subject can be a paediatric subject. The subject can be a healthy patient. The subject can be a subject that has been diagnosed having a disease or disorder or being likely to have a disease or disorder. In particular, the subject can be a subject that has been diagnosed with Alzheimer's disease, Parkinson's disease, MS, amyotrophic lateral sclerosis, Huntington's disease. In particular, the subject can be a subject likely to have Alzheimer's disease, Parkinson's disease, MS, amyotrophic lateral sclerosis, Huntington's disease. The received signals from one or more wearable sensors can be previously obtained while the subject is performing a single test or while the subject is performing a plurality of tests. The plurality of tests can be a plurality of tests of the same type or a plurality of tests comprising at least two different types of tests. Tests of the same type can be passive tests. Tests of the same type can be active tests. Tests of the same type can be 2MWT. The two different types of tests can be one active test and one passive test. The two different types of tests can be 2MWT and passive monitoring. The received signals can be previously obtained by tests performed by the subject repeatedly. The repeated tests can have been performed at regular intervals. The repeated tests can have been performed at random intervals. The received signals can be previously obtained in a supervised environment, for example a clinical setting. The received signals can be previously obtained in an unsupervised environment.

Signals from each sensor are divided into a plurality of signal blocks comprising the signal of the respective sensor over a time interval by at least dividing the signals from each sensor into a plurality of non-overlapping signal blocks and/or a plurality of signal blocks of a predetermined duration. The predetermined duration can be set as the mean step time of a reference population. The reference population can be a population of healthy individuals. From literature, the mean step time of a healthy population can be 0.5 seconds. The reference population can be a population diagnosed with a particular disease. The reference population can be a population monitored for a particular disease. The mean step time of a reference population diagnosed with a particular disease can be as high as 0.6/0.7 seconds, with a maximum value as high as 1.1 seconds.

The received signal can be processed by at least: classifying one or more of a plurality of signal blocks between a plurality of categories comprising at least a rest category and a non-rest category, the non-rest category comprising at least a straight-gait category, using the magnitude and/or standard deviation of the respective signal block; selecting one or more of a plurality of signal blocks classified as at least one of the plurality of categories. Directional components can be determined for one or more of the selected signal blocks.

The rest category can comprise a short-rest category and a long-rest category, based on a predetermined rest duration threshold. In particular, signal blocks in the short-rest category can comprise signal blocks in the rest category with a duration below the predetermined rest duration threshold and signal blocks in the long-rest category can comprise signal blocks in the rest category with a duration above the predetermined rest duration threshold. A suitable rest duration threshold can be 2 seconds. The method can further comprise merging signal blocks if spaced from each other below a predetermined time threshold. The merging of signal blocks spaced within the predetermined time threshold can serve to remove artifacts due to irregularity of the subject's movements throughout a test, in particular at the start and/or end of the test.

The non-rest category can comprise at least a straight-gait category. The straight-gait category can comprise signal blocks with gyroscope signal below a predetermined minimum threshold. A suitable minimum threshold of the angular velocity measured by the gyroscope can be 15 degrees per second. The method can further comprise classifying signal blocks in the non-rest category with a duration below a predetermined minimum duration as unknown blocks.

The method can further comprise classifying one or more of the plurality of signal blocks as boundary blocks. For example, signal blocks spaced from the start of the received signals or from the end of the received signals below a predetermined time threshold can be classified as boundary blocks. Spacing in this manner can serve to integrate the information about the context around a block.

According to a second aspect, the present disclosure provides a method according to the first aspect, further comprising calculating, for at least one of the plurality of signal blocks, a step frequency using the determined directional components of the signal block; selecting one of the determined directional components of the signal block using the calculated step frequency and the computed autocorrelations of each directional component; obtaining a continuous wavelet transform of the selected directional component; calculating at least a first derivative of the continuous wavelet transform, and optionally a second derivative of the continuous wavelet transform; extracting, from the calculated at least first derivative and optionally second derivative of the continuous wavelet transform, one or more gait features. The one or more extracted gait features can comprise: step duration, stride duration, step frequency, heel-strike events, toe-off events, stance-phase parameters (e.g., duration, average duration, frequency, average frequency, and/or the like), swing-phase parameters (e.g., duration, average duration, frequency, average frequency, and/or the like), indirect gait features. Indirect gait features can comprise, for example, the subject's cadence, fatigue, stability, rhythm/variability, asymmetry, pace, forward balance, lateral balance, and/or the like. In an embodiment, the method according to the second aspect can be performed for at least one of the one or more classified and selected signal blocks.

Using the determined directional components of the signal block to calculate step frequency comprises: computing a first antero-posterior autocorrelation of the antero-posterior component of the signal block; computing a second antero-posterior autocorrelation of the antero-posterior component of the signal block, wherein the second anterior-posterior autocorrelation includes an autocorrelation of the first anterior-posterior autocorrelation of the antero-posterior component; computing a first vertical autocorrelation of the vertical component of the signal block; computing a second vertical autocorrelation of the vertical component of the signal block, wherein the second vertical autocorrelation incudes an autocorrelation of the first vertical autocorrelation of the vertical component; computing a cross-correlation of the second antero-posterior autocorrelation of the antero-posterior component and of the second vertical autocorrelation of the vertical component; estimating the distance between peaks of the computed cross-correlation; calculating, using the estimated distance, the step frequency.

According to some example embodiments of the present disclosure, stride duration may be estimated by at least leveraging a second autocorrelation of a first autocorrelation of the directional components, followed by the operation of cross-correlation. For example, in some cases, the stride duration may be estimated based on an estimate of the distance between every other peak of the cross-correlation. Such estimation of the stride duration is more precise than the one obtained by using first autocorrelations only as state-of-the-art methods do (Moe-Nilssen et al, 2004), since first autocorrelations can contain noise and/or spurious peaks. The step frequency calculated from the stride duration so obtained is thus also more precise than in state-of-the-art methods. Alternatively, the step frequency can be calculated from an estimate of the step duration, wherein the estimate of the step duration is obtained from an estimate of the distance between every peak of the cross-correlation.

The continuous wavelet transform of the signals can allow the identification of heel-strike events as the minima of the first derivative of the continuous wavelet transform. The continuous wavelet transform of the signal can also allow the identification of toe-off events as the maxima of the second derivative of the continuous wavelet transform. In some embodiments of the present disclosure, the calculated step frequency can be functional to obtain the continuous wavelet transform, for example, to obtain the parameterized continuous wavelet function that is applied to the signal to perform the continuous wavelet transform of the signal. In particular, the step frequency can be used directly to identify the wavelet axis and the wavelet scale. The wavelet axis can define the direction in which the continuous wavelet function is applied to the signal. The wavelet axis can be identified as the direction of the directional component of the signal, which corresponds to the highest power spectral density in a neighborhood of the calculated step frequency. Furthermore, the wavelet scale can be computed as a function of the calculated step frequency.

The method can have one or more of the following features.

One of the determined directional components of the signal block can be selected using the calculated step frequency and the computed autocorrelations of each directional component. The selection can comprise: calculating a power spectral density for each autocorrelation of each directional component; selecting an interval comprising the calculated step frequency; and selecting the directional component with the highest power spectral density in the selected interval.

A continuous wavelet transform of the selected directional component can be obtained by at least obtaining a parameterized continuous wavelet function, and obtaining the parameterized continuous wavelet function can comprise estimating at least a wavelet scale and/or a wavelet sign. The wavelet scale can be a function of the calculated step frequency. Estimating a wavelet sign can comprise: computing a norm of the accelerometer signal in the signal block; computing a correlation of the parameterized continuous wavelet function and of the calculated norm; determining, based on the sign of the computed cross-correlation, the wavelet sign.

According to a third aspect, there is provided a method of diagnosing or monitoring a neurological dysfunction associated with gait activity in a subject, the method comprising: analyzing the gait activity of the subject using the method of any embodiment of the preceding aspects. The neurological dysfunction can be selected from: multiple sclerosis (MS), Parkinson's disease, Huntington's disease. The neurological dysfunction can be MS. Analyzing the gait activity can comprise determining one or more of: step duration, stride duration, step frequency, heel-strike events, toe-off events, stance-phase parameters (e.g. duration, average duration, frequency, average frequency, and/or the like), swing-phase parameters (e.g. duration, average duration, frequency, average frequency, and/or the like), indirect gait features. Indirect gait features can comprise for example the subject's cadence, fatigue, stability, rhythm/variability, asymmetry, pace, forward balance, lateral balance. It is proven in the literature that said gait features can provide diagnostic information for neurological dysfunctions (Angelini et al, 2021). Analyzing the gait activity can comprise determining one or more gait features (such as for example pace) and comparing the one or more gait features to one or more reference values. The one or more reference values can comprise an expected value of a gait feature associated with a healthy population (e.g. mean value previously determined for a healthy population). The one or more reference values can comprise an expected value of a gait feature associated with a diseased population (e.g. mean value previously determined for a diseased population). The one or more reference values can comprise a value of a gait feature previously obtained for the same subject.

According to a fourth aspect, there is provided a method of treating a subject for a neurological dysfunction, the method comprising: determining whether the subject has the neurological dysfunction using the method of any embodiment of the third aspect; and administering a therapeutically effective amount of a therapy for the treatment of the neurological dysfunction to the subject who has been determined as having the neurological dysfunction.

According to a further aspect, there is provided a system that includes a processor and a computer readable medium storing instructions that, when executed by the processor, cause the processor to perform at least a portion of the computer-implemented method of any preceding aspect. The system can further comprise means for acquiring signals associated with a gait activity of a subject from, for example, one or more wearable sensors. According to a further aspect, there is provided a non-transitory computer readable medium or media storing instructions that, when executed by at least one processor, cause the at least one processor to perform the method of any embodiment of any aspect described herein. According to a further aspect, there is provided a computer program comprising code which, when executed on a computer, causes the computer to perform the method of any embodiment of any aspect described herein.

BRIEF DESCRIPTION OF THE FIGURES

FIG. 5 is a flow diagram showing, in schematic form, an example of a method of selecting the wavelet axis of a continuous wavelet function, according to some example embodiments.

FIG. 6 is a flow diagram showing, in schematic form, an example of a method of estimating the wavelet sign of a continuous wavelet function, according to some example embodiments.

FIG. 7 is a summary figure showing the methods of the previous figures relative to each other, according to some example embodiments.

FIG. 8B shows an example of the sum of autocorrelations, the norm of autocorrelations, and the autocorrelation of the summed sum and norm, according to some example embodiments.

FIG. 9B shows an example of the cross-correlation of the two curves in FIG. 9a, according to some example embodiments.

DETAILED DESCRIPTION

Figure 1:
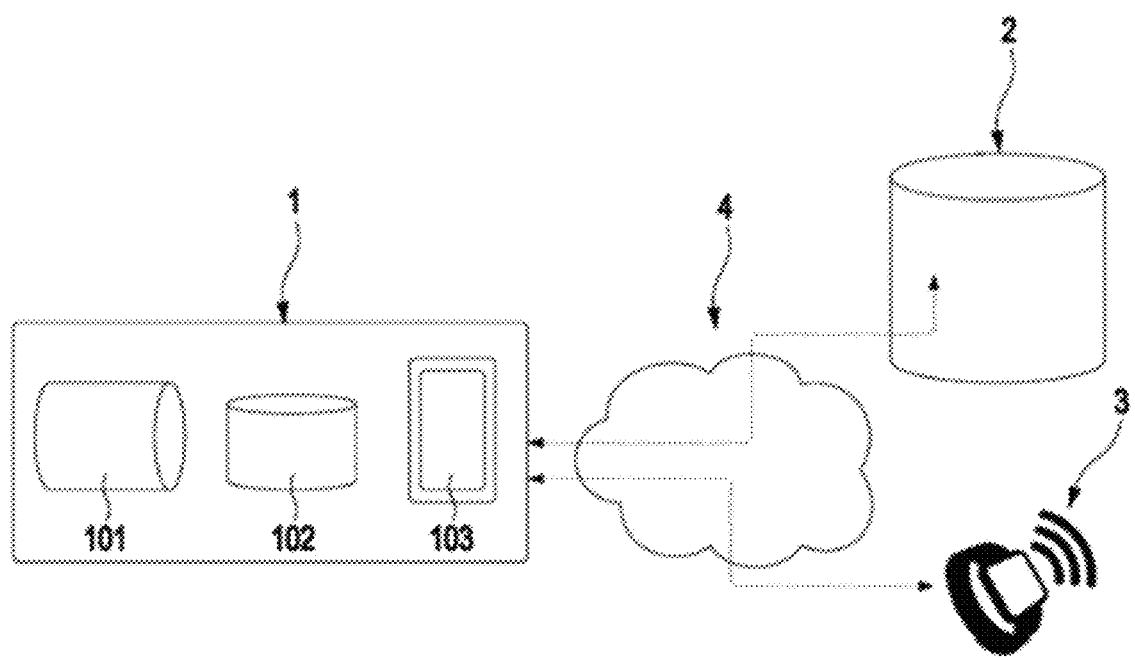
FIG. 1 illustrates an embodiment of a system that can be used to implement one or more aspects described herein.

In describing various embodiments of the present disclosure, the following terms will be employed, and are intended to be defined as indicated below.

A neurological dysfunction as used herein refers to a neurological condition or disorder that affects brain functions, in particular motor functions, including neurodevelopmental disorders, psychiatric disorders, neurodegenerative disorders. Examples of neurodegenerative disorders are Alzheimer's disease, Parkinson's disease, MS, amyotrophic lateral sclerosis, Huntington's disease.

The systems and method described herein can be implemented in a computer system, in addition to the structural components and user interactions described. As used herein, the term "computer system" includes the hardware, software and data storage devices for embodying a system and carrying out a method according to the described embodiments. For example, a computer system can comprise one or more central processing units (CPU) and/or graphics processing units (GPU), input means, output means and data storage, which can be embodied as one or more connected computing devices. Preferably the computer system has a display or comprises a computing device that has a display to provide a visual output display. The data storage can comprise RAM, disk drives, solid-state disks or other computer readable media. The computer system can comprise a plurality of computing devices connected by a network and able to communicate with each other over that network. It is explicitly envisaged that computer system can comprise a cloud computer. The wearable motion sensors or devices described herein can comprise sensors integrated into wearable objects, such as for example smartwatches, and/or into objects that can be carried by a subject, such as for example smartphones, tablets, laptops, Inertial Measurement Units (IMU), and/or directly within the body, such as for example subcutaneous chips. The wearable motion sensors described herein comprise an accelerometer and a gyroscope. The wearable motion sensors described herein are configured to transmit data to a computer system.

As used herein "data" and "signals" are used interchangeably unless otherwise specified.

The methods described herein are computer implemented unless context indicates otherwise. Indeed, the features of the data associated with gait activity are such that the methods described herein are far beyond the capability of the human brain and cannot be performed as a mental act. The methods described herein can be provided as computer programs or as computer program products or computer readable media carrying a computer program which is arranged, when run on a computer, to perform the method(s) described herein. As used herein, the term "computer readable media" includes, without limitation, any non-transitory medium or media which can be read and accessed directly by a computer or computer system. The media can include, but are not limited to, magnetic storage media such as floppy discs, hard disc storage media, magnetic tape; optical storage media such as optical discs or CD-ROMs; electrical storage media such as memory, including RAM, ROM and flash memory; hybrids and combinations of the above such as magnetic/optical storage media.

Figure 10:
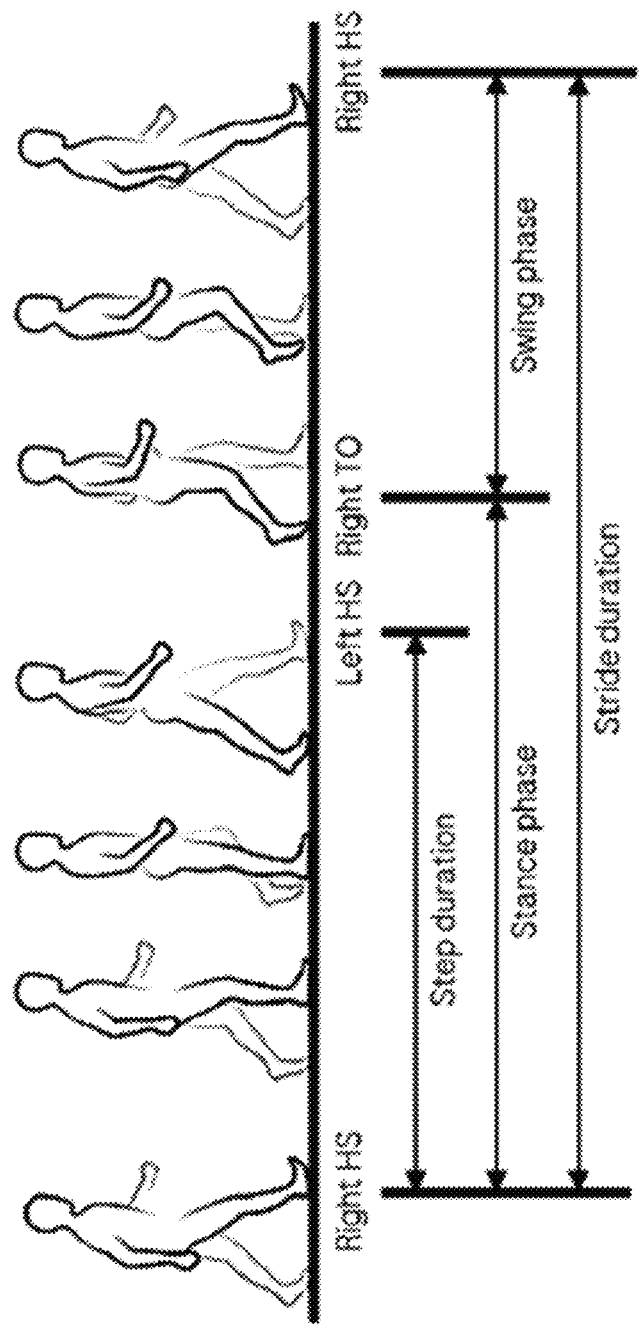
FIG. 10 illustrates a human gait cycle.

Various embodiments of the present disclosure relate to processing and/or statistical analysis of digital signals, for example to detect oscillatory patterns typical of gait activity. Gait activity as used herein refers to features of a plurality of gait cycles or fractions of a gait cycle. A gait cycle is a repetitive pattern consisting of a stance phase and a swing phase. The stance phase corresponds to the period of time when one foot is in contact with the ground. The swing phase corresponds to the period of time when one foot is not in contact with the ground. A human gait cycle is illustrated in FIG. 10. In normal human walking gait cycles, the stance phase counts for about 60% and the swing phase counts for about 40% of the gait cycle. The stance phase can be characterized by the following events for each foot: heel-strike (HS), foot-flat (FF), midstance, heel-off (HO), toe-off (TO). A HS event corresponds to the instant of initial contact of one foot with the ground. An FF event corresponds to the instant when the rest of the foot comes into contact with the ground. Midstance is defined when the center of mass is directly above the ankle joint center. A HO event corresponds to the instant when the heel begins to lift off the ground. A TO corresponds to the instant when the toe lifts off the ground. The swing phase for each foot begins with a TO and ends with a HS. Step length is the linear distance between the corresponding placements of right foot and left foot, for example the linear distance between a right-foot HS and a left-foot HS. Stride length is the linear distance between two successive placements of the same foot, e.g., two-step lengths or the linear distance between two successive right-foot HS. Step duration is the time used to complete the step length. Stride duration is the time used to complete the stride length, e.g., the full gait cycle duration equal to the stance phase duration plus the swing phase duration. Step frequency is inversely proportional to the step duration.

Figure 11:
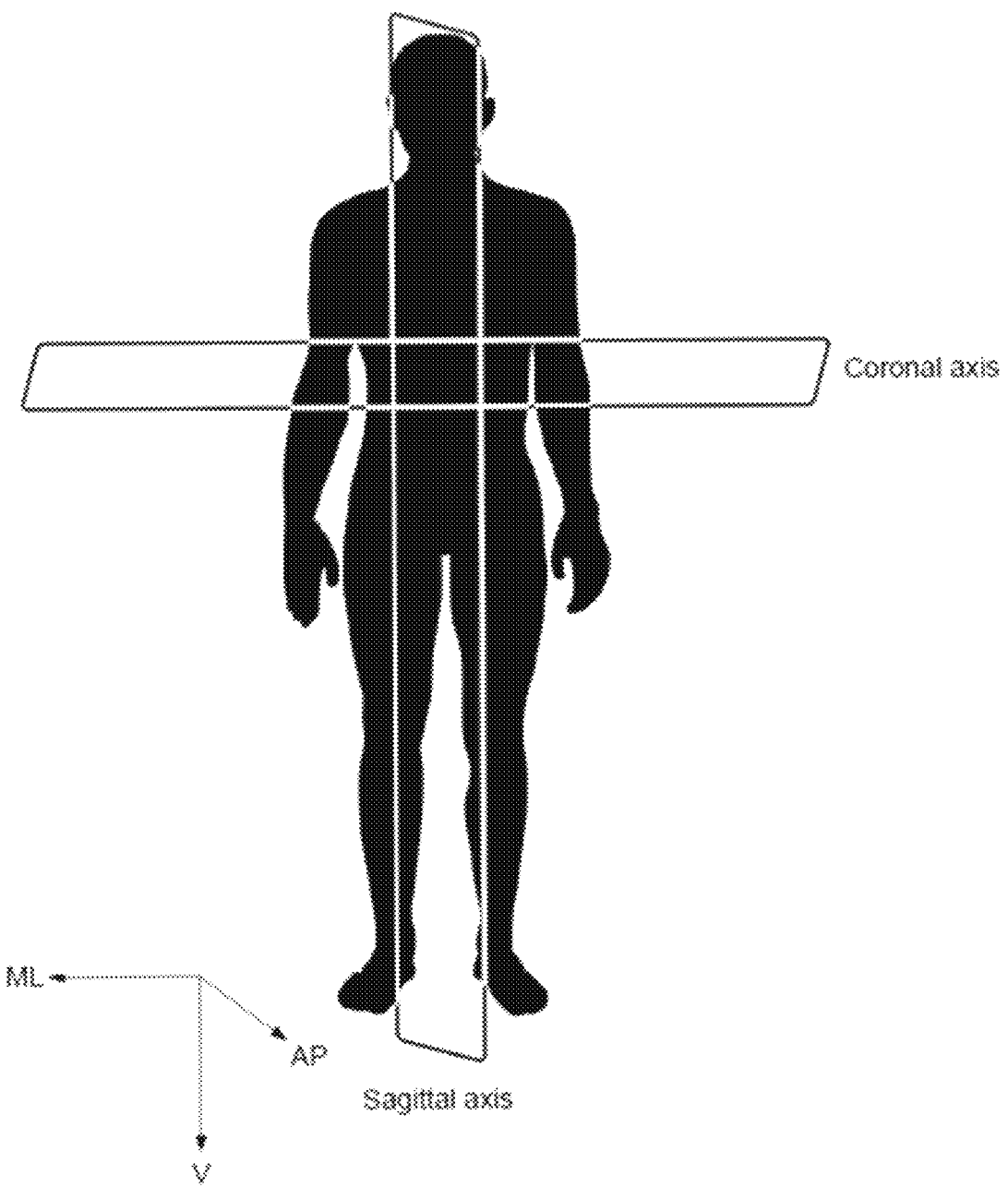
FIG. 11 illustrates the global walking directions.

As used herein and as shown in FIG. 11, the antero-posterior component of the signal is the projection of the signal on the antero-posterior direction, e.g., along the sagittal axis (or x-axis) in the body reference system. As used herein and as shown in FIG. 11, the medio-lateral component of the signal is the projection of the signal on the medio-lateral direction, e.g., along the coronal axis (or y-axis) in the body reference system. As used herein and as shown in FIG. 11, the vertical component of the signal is the projection of the signal on the vertical direction, e.g., the vertical axis (or z-axis) in the body reference system, aligned with the direction of gravity.

As used herein, autocorrelation is the correlation of a signal with a time-shifted instance of itself. The autocorrelation or autocorrelation curve or autocorrelation sequence of a periodic signal has the same cyclic characteristics as the signal itself. As used herein, cross-correlation is the correlation of two independent signals. The cross-correlation or cross-correlation curve or cross-correlation sequence is a measure of the similarity of two signals as a function of the displacement of one relative to the other. As used herein, distances or displacements referred to in autocorrelations or cross-correlations are temporal distances or time shifts. In the present disclosure, the time-shifted instance of the signal is obtained by shifting the signal by one sample time step. The sample time step depends on the signal sampling frequency: if for example the signal sampling frequency is 50 Hz, then the sample time step is 0.02 seconds. The signal sampling frequency can be the sampling frequency of the wearable device. The signal sampling frequency can be the frequency at which the signal from the wearable device is resampled.

As used herein, continuous wavelet transforms or continuous wavelet transformations are intended in their established mathematical definition. As used herein, continuous wavelet functions are functions applied to the signal to obtain a continuous wavelet transform of the signal. As used herein, power spectral density is intended as the measure of a signal's power content. As used herein, a signal's power content is equivalent to a signal's frequency content. Power spectral densities are measured as a function of the signal frequency.

Systems

FIG. 1 illustrates an embodiment of a system that can be used to implement one or more aspects described herein. The system comprises a computing device 1, which comprises a processor 101 and a computer readable memory 102. In the embodiment shown, the computing device 1 also comprises a user interface 103, which is illustrated as a screen but can include any other means of conveying information to a user such as e.g. through audible or visual signals. The computing device 1 is communicably connected, such as e.g. through a network, to signal acquisition means, such as one or more wearable motion sensors, and/or to one or more databases 2 storing signals from the one or more wearable motion sensors. The one or more databases 2 can further store one or more of: control data, parameters (such as e.g. thresholds derived from control data, parameters used for normalization, etc.), clinical and/or patient related information, etc. The computing device can be a smartphone, tablet, personal computer or other computing device. The computing device can be configured to implement a method of processing signals associated with gait activity of a subject, as described herein. In alternative embodiments, the computing device 1 is configured to communicate with a remote computing device (not shown), which is itself configured to implement a method of processing signals associated with gait activity of a subject, as described herein. In such cases, the remote computing device can also be configured to send the result of the method of processing signals associated with gait activity of a subject. Communication between the computing device 1 and the remote computing device can be through a wired or wireless connection, and can occur over a local or public network 4 such as e.g. over the public internet. The signal acquisition means 3 can be in wired connection with the computing device 1, or can be able to communicate through a wireless connection, such as e.g. through Wi-Fi and/or over the public internet, as illustrated. The connection between the computing device 1 and the signal acquisition means 3 can be direct or indirect (such as e.g. through a remote computer). The signal acquisition means 3 are configured to acquire signals from one or more wearable motion sensors located on a subject, for example accelerometer signals and/or gyroscope signals. In some embodiments, the acquired signals can have been subject to one or more preprocessing operations (e.g. normalizing and/or the like) prior to performing the methods described herein.

Methods

Figure 2A:
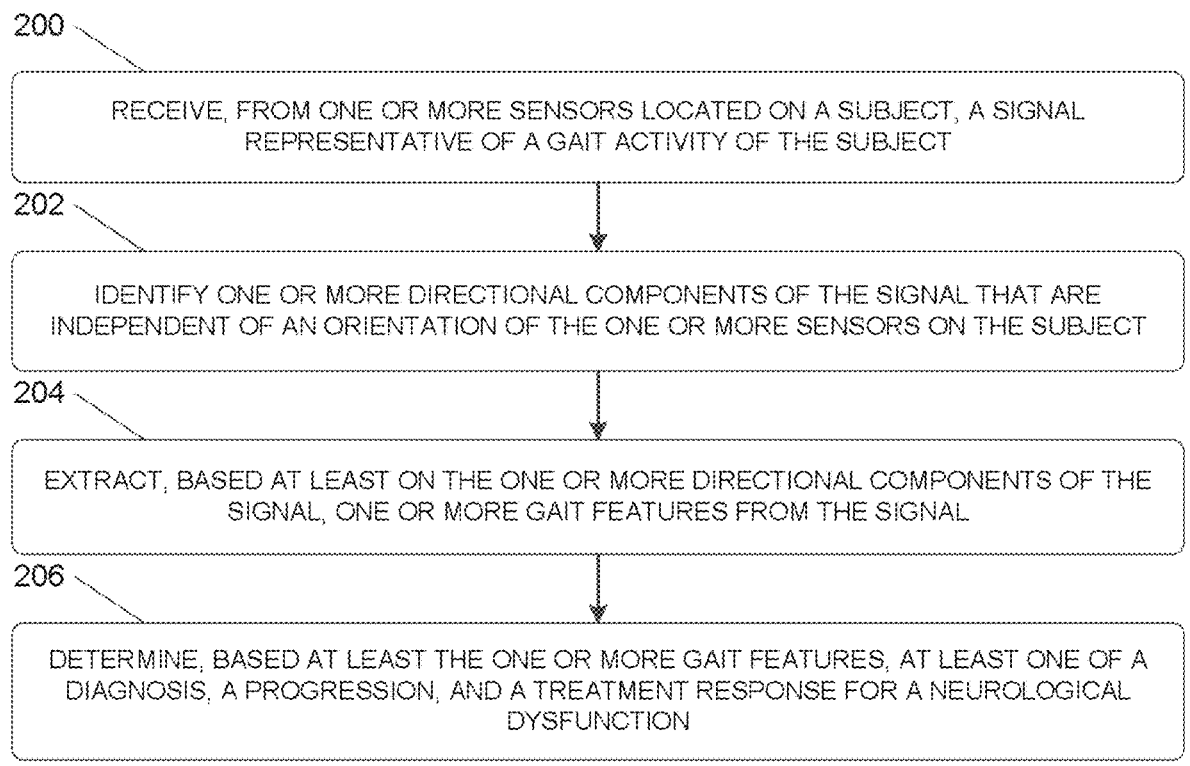
FIG. 2A is a flow diagram showing, in a schematic form, an example of a method for gait activity analysis with signals from one or more wearable motion sensors, in accordance with some example embodiments.

FIG. 2A is a flow diagram showing, in schematic form, an example of a method for gait activity analysis with signals from one or more wearable motion sensors, in accordance with some example embodiments. As shown in FIG. 2A, in some example embodiments, gait analysis for the diagnosis, monitoring, and/or treatment of a neurological dysfunction may be performed based on one or more gait features extracted based on the directional components of a signal generated by one or more wearable sensors located on a subject. For example, one or more gait features may be extracted from the signal based on one or more of a vertical component and a horizontal component of the signal before being assessed relative to one or more reference values. It should be appreciated that unlike the raw signal itself, the directional components of the signal are agnostic to the location and/or orientation of the wearable sensors generating the signal, which can vary due to a variety of factors (e.g., body shape and/or the like) that are extraneous to the objective of discriminating between normal and pathological gait. Thus, the gait features extracted from the directional components of the signal may provide a more accurate characterization of the subject's gait activity than those extracted from the raw signal. That is, the directional components of the signal, and the gait features extracted therefrom, do not vary due to the location and/or orientation of the wearable sensors. Instead, the differences in gait features extracted from the directional components of the signal are attributable to clinically meaningful variation in gait activity. Contrastingly, gait features extracted from the raw signal itself may vary depending on the location and/or orientation of the wearable sensors but this variability is noise in the context of gait analysis. Thus, using gait features extracted from the raw signal for gait analysis may prevent an accurate discrimination between normal and pathological gait. As described in more details below, these inaccuracies are eliminated if gait analysis is performed based on gait features extracted based on the directional components of the signal in accordance with various embodiments of the present disclosure.

Referring again to FIG. 2A, at 200, a signal representative of a gait activity of a subject is received from one or more sensors located on the subject. For example, in some cases, the computing device 1 may receive, from one or more wearable sensors located on a subject, a signal representative of a gait activity of the subject. In some cases, the signal can be received directly from the one or more wearable sensors. Alternatively, the signal can be previously recorded and received, for example from a memory or other computing devices. In some cases, this signal may include at least one of an accelerometer signal and a gyroscope signal. For example, in some cases, the signal may include one or more measurements from an accelerometer at a plurality of timepoints. The measurement for an individual timepoint may include a value corresponding to an instantaneous linear acceleration detected by the accelerometer relative to the frame of reference of the accelerometer. In some cases, the signal can also include one or more measurements from a gyroscope at a plurality of timepoints. The measurement at an individual timepoint can include a value corresponding to an instantaneous angular velocity detected by the gyroscope relative to the frame of reference of the gyroscope.

At 202, the signal is processed to identify one or more directional components of the signal that are independent of an orientation of the one or more sensors on the subject. In some example embodiments, the computing device 1 may process the signal from the one or more wearable sensors in order to identify one or more directional components of the signal, which are independent of the location and/or orientation of the one or more wearable sensors on the subject. That is, the directional components of the signal may remain consistent regardless of the location and/or orientation of the one or more wearable sensors generating the signal. Without the various processing described herein, the raw signal itself may be dependent on the location and/or orientation of the one or more wearable sensors at least because the location and/or orientation of the one or more wearable sensors define the frame of reference used by the sensors when performing measurements such as linear acceleration, angular velocity, and/or the like. Subsequent gait analysis may include an assessment of the gait features extracted from the signal relative to one or more reference values. Thus, in cases where the gait features are extracted from the raw signal, any misplacement or misalignment of the sensors can result in inaccurate gait analysis results if the frame of reference of the sensors deviates from that of the reference values. Contrastingly, extracting gait features from the signal based on the directional components of the signal, which are not affected by the location and/or orientation of the one or more wearable sensors, eliminates these inaccuracies from subsequent gait analysis.

In some example embodiments, the computing device 1 may process the signal by dividing the signal into a plurality of signal blocks. For example, in some cases, the signal from the one or more wearable sensors may be divided into a plurality of non-overlapping signal blocks. Alternatively and/or additionally, the signal from the one or more wearable sensors may be divided into a plurality of signal blocks having a predetermined duration such as, for example, the mean step time of a reference population (e.g., a healthy population, a population monitored for a disease, and/or the like). In some cases, each signal block may be classified, into a one plurality of categories, based on the magnitude and/or standard deviation of the signal (e.g., accelerometer signal, gyroscope signal, and/or the like) in the signal block. For instance, in some cases, the computing device 1 may classify a signal block into a rest category (e.g., as a rest block) or a non-rest category (e.g., as a non-rest block). In some cases, a rest block may be further classified as a long-rest block and a short-rest block. Meanwhile, a non-rest block may be further classified as a straight-gait block or a non-straight gait block. In some cases, a non-rest block may be classified as an unknown block if the duration of the non-rest block fails to satisfy one or more thresholds. To remove artifacts and other noise that may be present in the signal blocks, the computing device 1 may also merge two or more signal blocks spaced below a time threshold apart.

In some example embodiments, the computing device 1 may decompose the signal in one or more signal blocks into one or more constituent directional components such as one or more of a vertical component, a medio-lateral component, an antero-posterior component, and/or the like. In some cases, some but not all of the signal blocks may be selected for the identification of one or more constituent directional components. For example, in some cases, the computing device 1 may select the non-rest blocks but not the rest blocks for the identification of one or more directional components. Furthermore, in some cases, the computing device 1 may further select the straight-gait blocks but not the non-straight gait blocks for the identification of the one or more directional components.

In some example embodiments, the computing device 1 may decompose the signal in a signal block into one or more directional components such as the triad of orthogonal components in the global walking directions (e.g., a vertical component along the direction of gravity and a horizontal component that further includes an antero-posterior component along the direction of walking and a medio-lateral component that is orthogonal to the antero-posterior component). In some cases, the signal may be decomposed by applying a filter. For example, in some cases, the vertical component of the signal may be identified by the computing device 1 applying an orientation filter, such as a Madgwick filter and/or the like, to the signal. Alternatively and/or additionally, the signal may be decomposed by the application of certain statistical analysis techniques. For instance, in some cases, one or more horizontal components (e.g., antero-posterior component, medio-lateral component, and/or the like) of the signal may be estimated by the computing device 1 applying a statistical analysis technique such as, for example, Principal Component Analysis (PCA) and/or the like. In some cases, the one or more directional components of the signal in the signal block may also be estimated by the computing device 1 applying a sensor fusion algorithm. As described in more details, in some cases, before the one or more directional components are used to extract gait features from the signal, the computing device 1 may validate the one or more directional components of the signal based on, for example, one or more peaks present in the autocorrelations of each directional component.

At 204, one or more gait features are extracted from the signal based at least on the one or more directional components of the signal. In some example embodiments, the computing device 1 may determine, based at least on the directional components of the signal (e.g., in each individual signal block), one or more gait features of the subject's gait activity. Examples of gait features include step duration, stride duration, step frequency, heel-strike events, toe-off events, stance-phase parameters (e.g., duration, average duration, frequency, average frequency, and/or the like), and swing-phase parameters (e.g., duration, average duration, frequency, average frequency, and/or the like). In some cases, the computing device 1 may also derive, from the one or more gait features, one or more indirect gait features such as cadence, fatigue, stability, rhythm/variability, asymmetry, pace, forward balance, lateral balance, and/or the like.

In some example embodiments, the one or more gait features may be determined based on one or more of an autocorrelation and a cross-correlation of the one or more directional components of the signal. For example, in some cases, stride duration may correspond to the distance between the peaks of a cross-correlation between an anterior-posterior autocorrelation of the antero-posterior component of the signal and a vertical autocorrelation of the vertical component of the signal. In some cases, the aforementioned anterior-posterior autocorrelation and the vertical autocorrelation may be second autocorrelations, which are computed as the autocorrelation of the autocorrelation (e.g., first autocorrelation) of the corresponding directional component. It should be appreciated that the second autocorrelation may be less prone to noise and/or spurious peaks than the first autocorrelation, and may thus yield a more precise estimate of stride duration than state-of-the-art methodologies that rely on the first autocorrelation.

In some example embodiments, step frequency may be further used to detect one or more heel-strike events and toe-off events that occur during the signal block. For example, in some cases, the one or more heel-strike events and toe-off events may be detected based on a wavelet transform, such as a continuous wavelet transform, of the one or more directional components of the signal. In some cases, the wavelet transform may be applied to determine how much of a wavelet, or an individual wave-like oscillation, is present in the signal by at least convolving (or multiplying) the wavelet at successive timesteps across the signal. Doing so may enable the detection of local peaks and troughs in the signal that are indicative of toe-off and heel-strike events, which may in turn be used to determine various indirect gait features such as cadence, fatigue, stability, rhythm/variability, asymmetry, pace, forward balance, and lateral balance. In some cases, the scale (or dilation) of the wavelet may correspond to the aforementioned step frequency, which may vary across the duration of the signal and for different subjects. This is in contrast to conventional methodologies, which assume a fixed wavelet scale whose value is constant, proportional to a constant step frequency, or corresponding to the most dominant frequency in the power spectral density of the one or more directional components. It should be appreciated that a wavelet scale corresponding to the step frequency determined in accordance with the manner disclosed herein may yield more precise and accurate results than conventional methodologies that assume a fixed wavelet scale.

At 206, at least one of a diagnosis, a progression, and a treatment response for a neurological dysfunction may be determined based at least on the one or more gait features. In some example embodiments, the one or more gait features, which may characterize the gait activity of the subject, may be used to diagnose, monitor, and/or treat a neurological dysfunction such as Alzheimer's disease, Parkinson's disease, multiple sclerosis (MS), amyotrophic lateral sclerosis, Huntington's disease, and/or the like. For example, in some cases, the computing device 1 may assess the one or more gait features of the subject relative to one or more corresponding reference values, which may be associated with a reference population such as a healthy population, a diseased population, and/or the like. Alternatively and/or additionally, the one or more reference values may be associated with one or more previous gait features obtained from the same subject at a different timepoint. In some cases, at least one treatment for the neurological dysfunction, including a type of treatment, a therapeutically effective amount of treatment, and/or a timing of treatment, may be identified based on the one or more gait features.

Figure 2B:
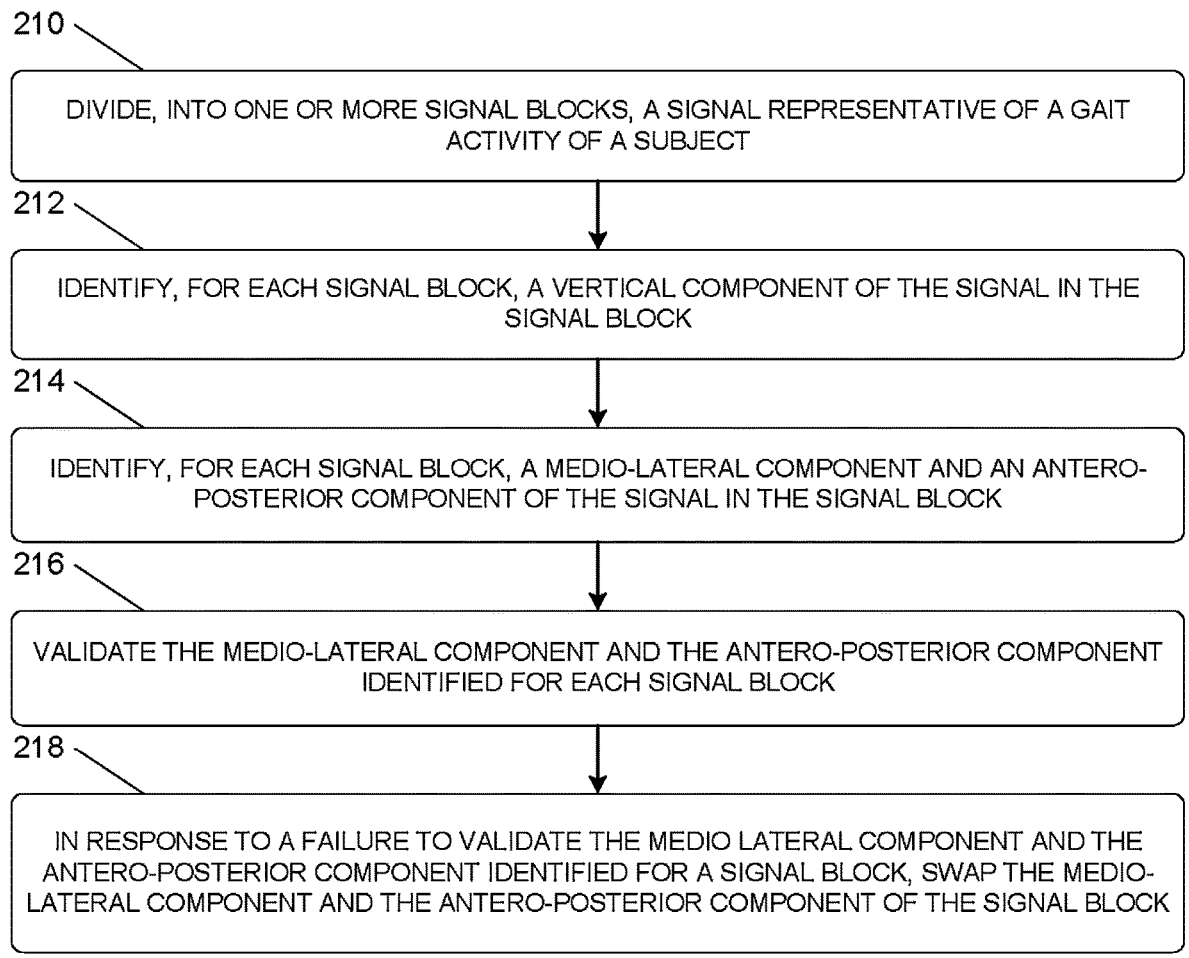
FIG. 2B is a flow diagram showing, in a schematic form, an example of a method for processing a signal representative of gait activity, in accordance with some example embodiments.

FIG. 2B is a flow diagram showing, in schematic form, an example of a method for processing signals from one or more wearable motion sensors, according to some example embodiments. Referring to FIGS. 2A and B, in some cases, the method shown in FIG. 2B may implement operation 202 of the method shown in FIG. 2A. For example, in some cases, the computing device 1 may perform the method shown in FIG. 2B in order to process a signal received from one or more sensors located on a subject. As described in more details below, the method shown in FIG. 2B may be performed in order to identify, within the signal received from the one or more sensors, one or more directional components that are independent of the orientation of the one or more sensors on the subject. Doing so may increase the accuracy of gait analysis performed based on gait features extracted from the signal based on the one or more directional components. As noted, gait features extracted from the raw signal itself may vary due to extraneous factors such as the location and/or orientation of the sensors, which means using gait features extracted from the raw signal for gait analysis may include noise that thwarts an accurate discrimination between normal and pathological gait. Contrastingly, because the directional components of the signal are unbiased by the orientation and/or location of the sensors generating the signals, the gait features extracted therefrom may accurately characterize the subject's gait activity.

At 210, a signal representative of a gait activity of a subject is divided into one or more signal blocks. In some example embodiments, the computing device 1 may divide a signal received from the signal acquisition means 3 into one or more signal blocks of a predetermined duration such as, for example, the mean step time of a reference population (e.g., a healthy population, a population monitored for a disease, and/or the like). In some cases, the computing device 1 may classify each signal block into a category such as, for example, a rest category (e.g., a long-rest category or a short-rest category), a non-rest category (e.g., a straight-gait category or a non-straight gait category), and/or the like. Furthermore, in some cases, the computing device 1 may select, based at least on the category assigned to each signal, some but not all of the signal blocks for further processing to identify one or more constituent directional components. For instance, in some cases, the computing device 1 may select one or more non-rest blocks or, even more specifically, straight-gait blocks, for further processing to identify one or more constituent directional components.

In some example embodiments, a signal block may be assigned to one or more categories based at least on whether the magnitude of the signal in the signal block satisfies one or more thresholds. For example, in some cases, the one or more sensors generating the signal may include an accelerometer and a gyroscope. In some cases, the signal block may be assigned to one or more categories based at least on whether the magnitude of the accelerometer signal in the signal block and the magnitude of the gyroscope signal in the signal block satisfies one or more thresholds. For instance, in some cases, the computing device 1 may determine, for each of the accelerometer signal and the gyroscope signal in the signal block, a summarized metric such as a mean, a median, a maximum, a minimum, a percentile, and/or the like. In some cases, the computing device 1 may classify the signal block as either a rest block or a non-rest block depending on whether the magnitude of the signal block's accelerometer signal (or the corresponding summarized metric) satisfies a threshold that quantifies how close the magnitude is to the acceleration of gravity g. Alternatively and/or additionally, the computing device 1 may classify the signal block as a rest block or a non-rest block depending on whether the magnitude of the signal block's gyroscope signal (or the corresponding summarized metric) satisfies a threshold that quantifies the rotational speed of the sensor, with a tolerance for small movements corresponding to the type of gait analysis (e.g., low tolerance for Static Balance Test (SBT) and high tolerance for 2-Minute-Walking-Test (2MWT)). In some cases, a non-rest block can be further classified, based on the presence of non-negligible motion (e.g., motion of a threshold magnitude) in a single or multiple directions of motion, as either a straight-gait block or a non-straight gait block. Moreover, a rest-block may be further classified, based on the duration of rest, as either a long-rest block or a short-rest block.

At 212, a vertical component of the signal is identified for each signal block. In some example embodiments, the computing device 1 may apply a filter, such as an orientation filter (e.g., Madgwick filter and/or the like), to a signal block from the signal in order to identify a vertical component of the signal. In some cases, the one or more directional components of the signal in the signal block, including the aforementioned vertical component, may also be estimated by the computing device 1 applying a sensor fusion algorithm.

At 214, a medio-lateral component and an antero-posterior component of the signal are identified for each signal block. In some example embodiments, the computing device 1 may apply a statistical analysis technique (e.g., Principal Component Analysis (PCA) and/or the like) or a sensor fusion algorithm in order to identify one or more horizontal components of the signal in the signal block. As noted, the horizontal components of the signal may include an antero-posterior component along the direction of walking and a medio-lateral component that is orthogonal to the antero-posterior component. As described in more details below, in some cases, the horizontal components of the signal may undergo validation at least because the two orthogonal horizontal components of the signal may be confounded, with the medio-lateral component being misidentified as the antero-posterior component and the antero-posterior component being misidentified as the medio-lateral component.

At 216, the medio-lateral component and the antero-posterior component identified for each signal block are validated. In some example embodiments, the horizontal components of a signal block, which are identified in the preceding operation 214, may be validated in order to avoid the medio-lateral component being misidentified as the antero-posterior component and the antero-posterior component being misidentified as the medio-lateral component. In some cases, the horizontal components of the signal block may be validated based on one or more peaks present in the autocorrelations of the horizontal components. It should be appreciated that the horizontal components are validated if these peaks are consistent with the biphasic nature of the antero-posterior component and the monophasic nature of the medio-lateral component. For example, to validate the horizontal components of the signal in the signal block, the computing device 1 may determine a medio-lateral autocorrelation of the medio-lateral component of the signal and an antero-posterior autocorrelation of the antero-posterior component of the signal. In some cases, the horizontal components of the signal may be validated as correctly identified if the autocorrelation of the biphasic antero-posterior component shows a first positive peak while the autocorrelation of the monophasic medio-lateral component is showing a first negative peak. If the first peaks of the autocorrelation of both horizontal components are negative, the first peak of the antero-posterior component should exhibit the highest absolute value, given that the main direction of motion is along the antero-posterior component (e.g., forward/backward). Contrastingly, the horizontal components of the signal are incorrectly identified if the antero-posterior autocorrelation of the antero-posterior component shows a first negative peak while the medio-lateral autocorrelation of the medio-lateral component is showing a first positive peak. The horizontal components of the signal may also be incorrectly identified if, when the first peaks of the autocorrelation of both horizontal components are negative, the medio-lateral autocorrelation of the medio-lateral component is highest in absolute value instead of the first peak of the antero-posterior autocorrelation of the antero-posterior component.

At 218, the medio-lateral component and the antero-posterior component identified for a signal block are swapped in response to a failure to validate the medio-lateral component and the antero-posterior component of the signal block. In some example embodiments, the computing device 1 may fail to validate the horizontal components of the signal block if the first peak of the autocorrelation of the biphasic antero-posterior component is negative while the first peak of the autocorrelation of the monophasic medio-lateral component positive. Alternatively, the computing device 1 may fail to validate the horizontal components of the signal block if the first peak of the medio-lateral component exhibits the highest absolute value when the first peaks of both horizontal components are negative. It should be appreciated that in cases where the computing device 1 fails to validate the horizontal components of the signal block, the computing device 1 may detect a misidentification of the horizontal components in which the medio-lateral component is misidentified as the antero-posterior component and the antero-posterior component is misidentified as the medio-lateral component. Accordingly, the computing device 1 may, upon failing to validate the horizontal components of the signal block, swap the medio-lateral component and the antero-posterior component identified for the signal block.

Figure 2C:
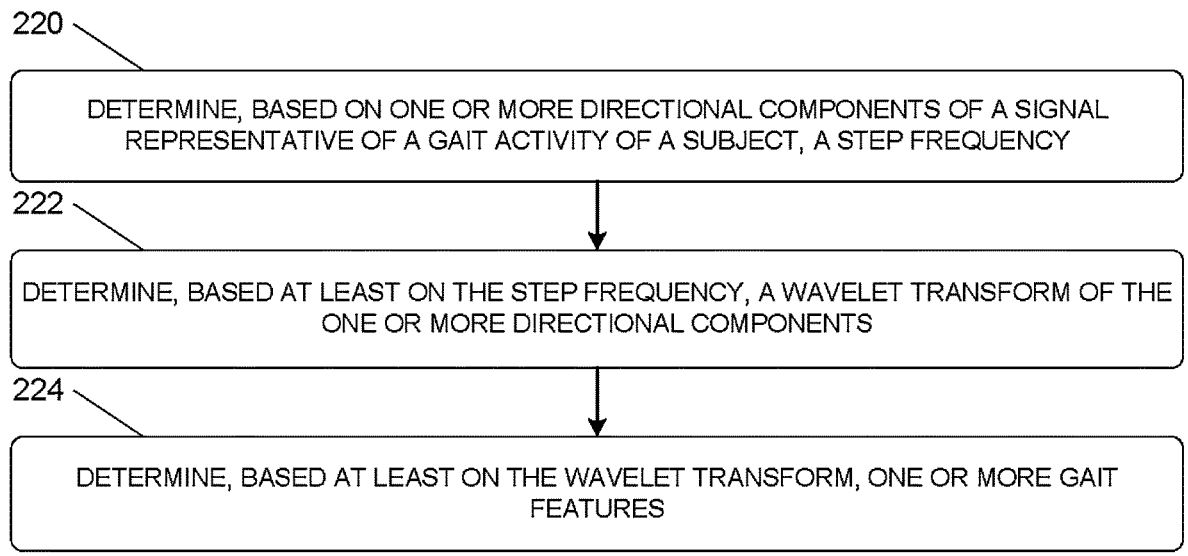
FIG. 2C is a flow diagram showing, in a schematic form, an example of a method for extracting gait features, in accordance with some example embodiments.

FIG. 2C is a flow diagram showing, in a schematic form, an example of a method for extracting gait features from a signal based on one or more directional components of the signal, according to some example embodiments. Referring to FIGS. 2A and C, in some cases, the method shown in FIG. 2C may implement operation 204 of the method shown in FIG. 2A. For example, in some cases, the method shown in FIG. 2C may be performed to extract, from a signal received from one or more sensors located on a subject, one or more gait features indicative of a gait activity of the subject. As described in more details below, instead of extracting gait features from the raw signal, the gait features may be extracted from the directional components of the signal including, for example, one or more of a vertical component, medio-lateral component, antero-posterior component, and/or the like. Because the directional components of the signal are independent of the location and/or orientation of the sensors on the subject, the gait features extracted therefrom may be unbiased by any misplacement or misalignment of the sensors. Accordingly, gait analysis using gait features extracted from the directional components of the signal may yield more accurate results for the diagnosis, monitoring and treatment neurological dysfunctions.

At 220, a step frequency may be determined based on one or more directional components of a signal representative of a gait activity of a subject. In some example embodiments, the computing device 1 may determine, based on one or more vertical and horizontal components of the signal received from the signal acquisition means 3, a step frequency. In some cases, the computing device 1 may determine the step frequency based at least on a cross-correlation of the autocorrelations of each a vertical component and a horizontal component (e.g., antero-posterior component) of the signal. For example, the computing device 1 may compute a first horizontal autocorrelation of a horizontal component of the signal, such as a first antero-posterior autocorrelation of the antero-posterior component of the signal. Furthermore, the computing device 1 may compute a first vertical autocorrelation of the vertical component of the signal. In some cases, the computing device 1 may further compute a second horizontal autocorrelation of the first horizontal autocorrelation and a second vertical autocorrelation of the first vertical autocorrelation. The second autocorrelations may be used for calculating the step frequency instead of the first autocorrelations at least because the second autocorrelations are less prone to exhibit noise and spurious peaks than the first autocorrelations. Accordingly, in some cases, the computing device 1 may calculate the step frequency by computing a cross-correlation of the second horizontal autocorrelation and the second vertical autocorrelation. The step frequency may correspond to the distance between two or more peaks in the cross-correlation of the second horizontal autocorrelation and the second vertical autocorrelation.

At 222, a wavelet transform of the one or more directional components may be determined based on the step frequency. In some example embodiments, the computing device 1 may determine a wavelet transform (e.g., continuous wavelet transform) of one directional component of the signal. In some cases, the wavelet transform of the directional component of the signal may be obtained by convolving (or multiplying) a wavelet (e.g., a single wavelike oscillation) at successive timepoints across the directional component. As described in more details below, the axis (or direction) of the wavelet, which refers the directional component to which the wavelet is applied, and the scale (or dilation) of the wavelet may be determined based on the step frequency computed in operation 220.

In some example embodiments, the scale (or dilation) of the wavelet may correspond to the step frequency, meaning that the width of the wavelet may correspond to a signal having the step frequency. Furthermore, in some cases, the computing device 1 may generate the wavelet transform by applying the wavelet to a directional component having the highest power in a frequency interval of the step frequency. That is, the axis (or direction) of the wavelet may be the one directional component having a higher power in the frequency interval of the step frequency than the other directional components of the signal. For example, in some cases, the computing device 1 may calculate, for each directional component of the signal, a corresponding power spectral density. The power spectral density of a directional component may describe the power of each frequency in a discrete or continuous frequency spectrum. In some cases, the computing device 1 may select a frequency interval that includes the step frequency such as, for example, a range of frequencies within +/−25% (or within +/−10%, +/−15%, +/−25%, or +/−30%) of the calculated step frequency. The one directional component with the highest power in the selected frequency interval than the other directional components of the signal may be identified as the axis (or direction) of the wavelet. For instance, if the vertical component of the signal exhibits a higher power in the frequency interval of the step frequency than the horizontal components of the signal, the computing device 1 may generate a wavelet transform (e.g., continuous wavelet transform) of the vertical component by at least convolving a wavelet whose scale (or dilation) corresponds to the step frequency at successive timepoints across the vertical component of the signal.

At 224, one or more gait features may be determined based at least on the wavelet transform. In some example embodiments, the computing device 1 may determine, based at least on the wavelet transform obtained in operation 222, one or more gait features characteristic of the gait activity of the subject. In some cases, one or more of a toe-off event and a heel-strike events may be identified based on the wavelet transform (e.g., continuous wavelet transform) of the directional component having the highest power in the frequency interval of the step frequency. For example, in some cases, the computing device 1 may identify a heel-strike event as the minimum of a first derivative of the wavelet transform and a toe-off event as the maximum of a second derivative of the wavelet transform. In some cases, a variety of gait features may be determined based on the one or more of the heel-strike event and the toe-off event. For instance, in some cases, the computing device 1 may determine, based at least on the timing and/or location of the one or more of the heel-strike event and toe-off event, one or more gait features characteristic of the gait activity of the subject. Examples of such gait features include cadence, fatigue, stability, rhythm/variability, asymmetry, pace, forward balance, lateral balance, and/or the like. In some cases, the computing device 1 may further determine, based at least on the one or more gait features, at least one of a diagnosis, a progression, and a treatment response for a neurological dysfunction such as Alzheimer's disease, Parkinson's disease, multiple sclerosis (MS), amyotrophic lateral sclerosis, Huntington's disease, and/or the like.

Figure 2D:
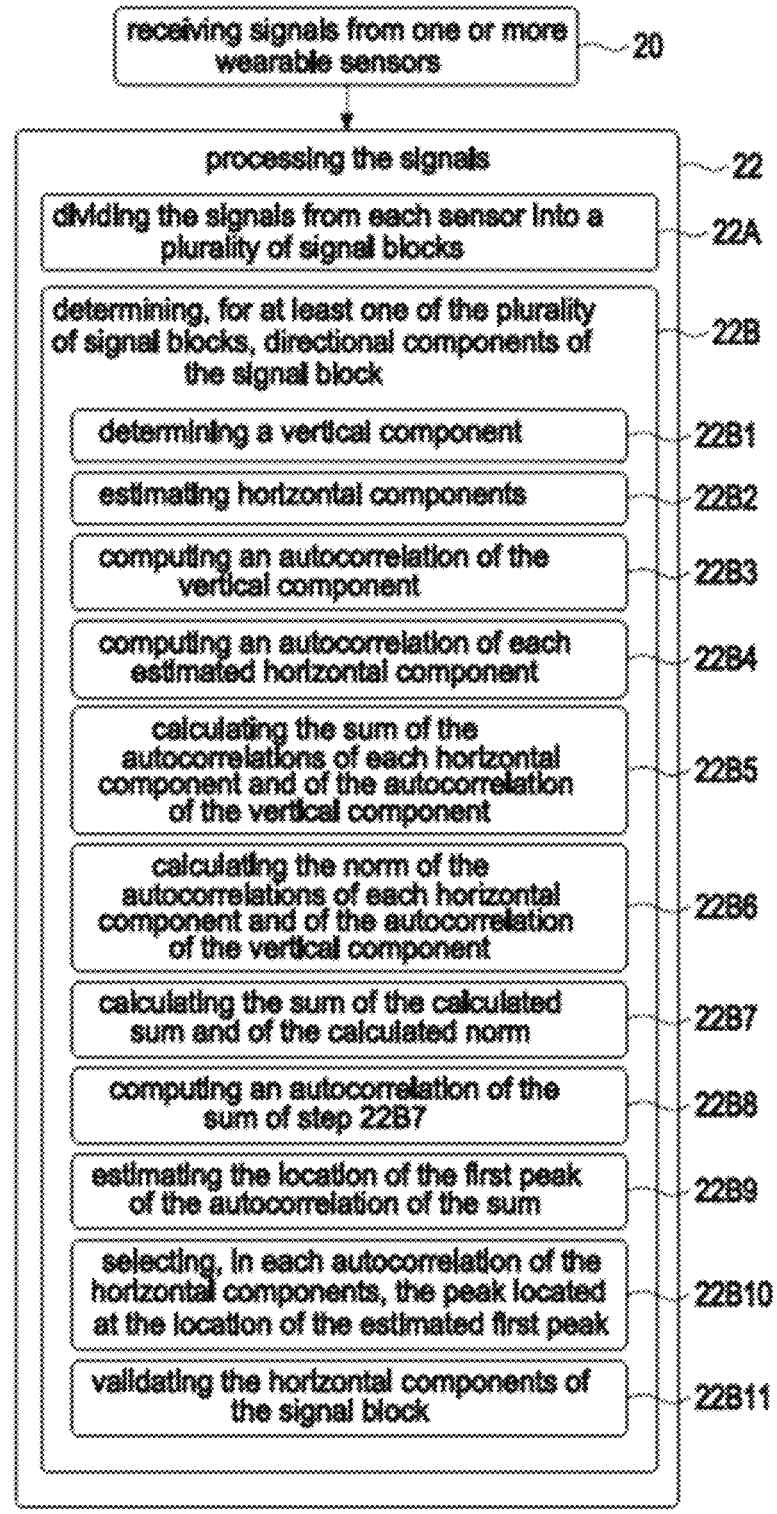
FIG. 2D is a flow diagram showing, in schematic form, another example of a method of processing signals from one or more wearable motion sensors to analyze gait activity of a subject, according to some example embodiments.

FIG. 2D is a flow diagram showing, in schematic form, another example of a method of processing signals from one or more wearable motion sensors to analyze gait activity of a subject, according to some example embodiments. With reference to FIG. 2D, at step 20, signals from one or more wearable sensors are received. This comprises receiving accelerometer signals and gyroscope signals. Signals can be received directly from the sensors. Signals can have been previously recorded and received, for example from a memory or other computing devices. In an embodiment, signals can comprise measurements from an accelerometer at a plurality of time points. The measurements can comprise values of a measured instantaneous acceleration of the sensor relative to its frame of reference. The frame of reference of the sensor can be a frame of reference associated with the sensor. In an embodiment, signals can comprise measurements from a gyroscope at a plurality of time points. The measurements can comprise values of a measured instantaneous acceleration of the sensor relative to its frame of reference. The frame of reference of the sensor can be a frame of reference associated with the sensor. At step 22, the signals are processed. Processing can comprise several steps performed for each received signal, in the order as follows or in other orders. At step 22A, the signals from each sensor are divided into a plurality of signal blocks. For example, said signal blocks can be non-overlapping blocks and/or signal blocks of a predetermined duration. This step can comprise the step of classifying one or more of the plurality of signal blocks between a plurality of categories. The plurality of categories can comprise at least a rest category and a non-rest category. The non-rest category can comprise at least a straight-gait category. One or more of the plurality of blocks can be classified in one or more of the plurality of categories using a summarized metric over the block of the block's accelerator signal magnitude and/or of the block's gyroscope signal magnitude, and/or of the block's signal standard deviation. A summarized metric can be for example a mean, a median, trimmed versions thereof, maximum, minimum, percentile, suitably a median. The block's accelerator signal magnitude can be compared to a threshold that quantifies how close the magnitude is to the acceleration of gravity g. For example, the threshold can apply to the maximum difference between the accelerometer signal magnitude and the acceleration of gravity. For example, a threshold of 0.1 (or any other value x smaller than 0.5) may be used, such that the accelerometer signal magnitude is below the threshold if it is between 0.9 g (or (1−x)g) and 1.1 g (or (1+x)g)—where g is the acceleration of gravity. The acceleration of gravity g can be set equal to 9.81 m/s$^2$ with a precision of 2 decimals. Other choices of precision for the value of 830 g can be made. When the accelerometer signal magnitude is below the threshold, the block can be classified as a rest block. The block's gyroscope signal magnitude can be compared to a threshold that quantifies the rotational speed of the sensor. For example, a suitable range of the gyroscope signal threshold can be between 0.2 rad/s and 0.6 rad/s. If a threshold of 0.2 rad/s is chosen, the tolerance for possible small movements is low. If a threshold of 0.6 rad/s is chosen, the tolerance for possible small movements is high. In particular, a low tolerance for small movements can be set in a Static Balance Test (SBT). In particular, a high tolerance for small movements can be set in a 2MWT (2-Minute-Walking-Test). The block's signal standard deviation can be compared to a threshold that quantifies the average spread of signal standard deviations around the block signal mean over the blocks within the same category. A suitable threshold can be the pooled standard deviation over the blocks within the same category. If the block's signal standard deviation is below said threshold, the block is classified as a rest block. If the block's signal standard deviation is above said threshold, the block is classified as a non-rest block. For example a suitable range of the signal standard deviation threshold can be between 0.05 and 0.4, with 0.05 being the limit of rejecting static balance and 0.4 being a value tolerant of small movements. Each signal block can be classified depending on one criterion, or a plurality of criteria. For example, if a signal block is classified as a rest block in two out of the three conditions on the three parameters, then the block is classified as a rest block. Alternatively, if the block is classified as a rest block in all three conditions on the three parameters, then the block is classified as a rest block. Non-rest blocks can be further classified in straight-gait blocks and non-straight-gait blocks. Straight-gait blocks can be defined as blocks in which only movements in a single direction of motion are non-negligible. For example, straight-gait blocks can be signal blocks recording a straight walking streak. Non-straight-gait blocks can be defined as signal blocks wherein movements in more than one direction of motion have non negligible magnitude. For example, non-straight-gait blocks can be signal blocks encoding a U-turn. This step can comprise selecting one or more of a plurality of signal blocks classified as at least one of the plurality of categories. For example, signal blocks can be selected that are classified both as non-rest blocks and straight-gait blocks. Alternatively, signal blocks can be selected that are classified either as non-rest blocks, independently of whether they are straight-gait blocks, or as non-straight gait blocks. At step 22B, for at least one of the plurality of signal blocks, directional components of the signal block are determined. This step comprises the following steps, either in the following order or in another order: determining a vertical component (22B1), estimating horizontal components (22B2), computing an autocorrelation of the vertical component (22B3), computing an auto-correlation of each of the estimated horizontal components (22B4), calculating the sum of the autocorrelation of each horizontal component and of the autocorrelation of the vertical component (22B5), calculating the norm of the autocorrelation of each horizontal component and of the autocorrelation of the vertical component (22B6), calculating the sum of the calculated sum of autocorrelations and of the calculated norm of autocorrelations (22B7), computing an autocorrelation of the sum calculated in the previous step (22B8), estimating the location of the first peak of the autocorrelation of the sum (22B9), selecting in each autocorrelation of the horizontal components the peak located at the location of the first peak estimated in the previous step (22B10), validating the horizontal components of the signal block (22B11). Step 22B can further comprise a resampling of the signals to a predetermined sampling frequency. A suitable sampling frequency can be 50 Hz. At step 22B1, the vertical component can be obtained by applying an orientation filter to the signals. For example, a Madgwick filter can be applied. At step 22B2, the horizontal components can be estimated by statistical analysis procedures, such as for example Principal Component Analysis (PCA). The directional components can be estimated via a sensor fusion algorithm. Steps 22B3 and 22B4 can further comprise filtering the autocorrelations to remove spurious peaks and obtain sinusoidal autocorrelations. For example, the signals can be filtered using a $2^{nd}$ order Butterworth low-pass filter. The filter can have a cut-off frequency to select the low-frequency spectrum, wherein harmonic frequencies related to gait activity mainly appear. A suitable cut-off frequency can be 6 Hz. At step 22B5, the sum of the autocorrelations of the directional components is calculated as follows (Equation 1):

$$SUM = auto_{AP} + auto_{ML} + auto_V$$

wherein V stands for vertical, AP for antero-posterior, ML for medio-lateral. At step 22B6, the norm of the autocorrelations of the directional components is calculated as follows (Equation 2):

$$NORM = \sqrt{(auto_{AP}^2 + auto_{ML}^2 + auto_V^2)}$$

At step 22B7, the sum of the sum of autocorrelations and of the norm of autocorrelations is calculated as follows (Equation 3):

$$\Sigma = SUM + NORM$$

At step 22B8, the autocorrelation of the sum Σ calculated at step 22B7 is performed. Step 22B8 can comprise a filtering of the autocorrelation to obtain a smoother curve. A suitable filter can be a Savitzky-Golay (savgol) filter. At step 22B9, the location of the first peak of the autocorrelation is estimated. The first peak is defined as the first maximum from the start of the autocorrelation curve. Step 22B9 can comprise removing peaks with a duration above a predetermined minimum. Step 22B9 can comprise removing peaks with a duration below a predetermined maximum. Step 22B9 can comprise removing peaks with a duration above a predetermined minimum and below a predetermined maximum. From the literature, a duration smaller than 0.3 seconds can correspond to a running pace. Therefore the predetermined minimum can be 0.3 seconds. From the literature, a duration longer than 1.1 seconds can correspond to a maximum walking pace of a non-healthy subject. Therefore the predetermined maximum can be 1.1 seconds. At step 22B10, the location of the first peak obtained at step 22B9 is used to select the peaks in the autocorrelation curves at the same location estimated at step 22B9. At step 22B11, the selected peaks are used to validate the estimated horizontal components of the signal block. One or more predetermined criteria that apply to the signs of the selected peaks of each autocorrelation of the horizontal components are used to validate the estimated horizontal components. For example, the horizontal components can be correctly identified if: the selected peak of the antero-posterior component is positive and the selected peak of the medio-lateral component is negative; or the selected peak of the antero-posterior component and the selected peak of the medio-lateral component are negative and the selected peak of the antero-posterior component is the highest in absolute value. For example, the horizontal components can be incorrectly identified if: the selected peak of the antero-posterior component is negative and the selected peak of the medio-lateral component is positive; or the selected peak of the antero-posterior component and the selected peak of the medio-lateral component are negative and the selected peak of the medio-lateral component is the highest in absolute value. If at step 22B11 it is verified that the horizontal components are incorrectly identified, the two incorrectly identified components are swapped.

Figure 3:
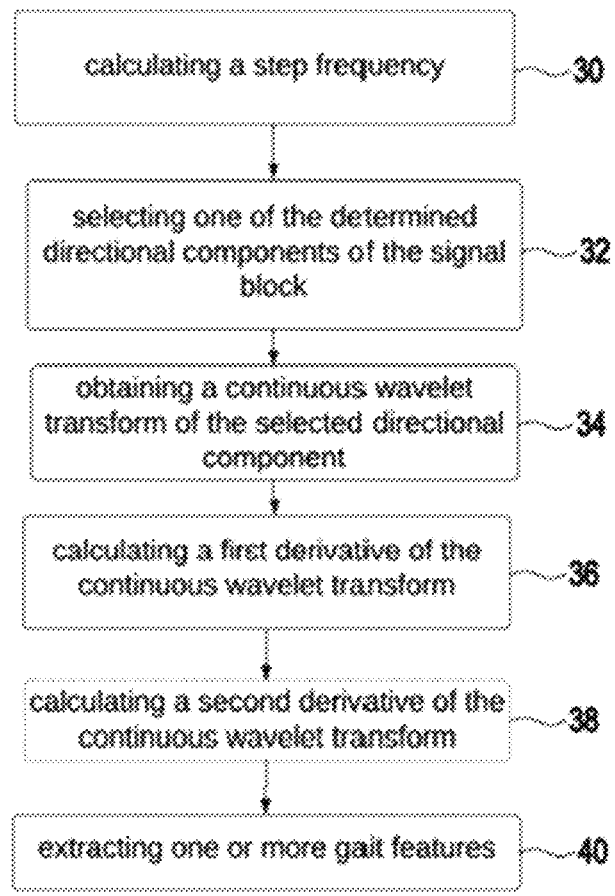
FIG. 3 is a flow diagram showing, in schematic form, another example of a method of extracting one or more gait features, according to some example embodiments.

FIG. 3 is a flow diagram showing, in schematic form, a method of extracting one or more gait features, according to some example embodiments. This method can be performed after the method of FIG. 2D. With reference to FIG. 3, at step 30 a step frequency is calculated for at least one of the one or more signal blocks, selected as described in FIG. 2D. The step frequency is calculated using the directional components of the signal block, determined as described in FIG. 2D. At step 32, one of the determined directional components of the signal block is selected using the calculated step frequency and the autocorrelations of each directional component, computed as described in FIG. 2D. At step 34, a continuous wavelet transform of the selected directional component is obtained. A general mathematical expression of a continuous wavelet transform is the following (Equation 4):

$$X_\omega(a, b) = \frac{1}{|a|^{1/2}} \int_{-\infty}^{\infty} x(t) \overline{\psi}\left(\frac{t-b}{a}\right) dt$$

wherein x(t) corresponds to the selected directional component, $\psi$ is the continuous wavelet function, t is the time, a is a parameter defining the scale (or dilation) of each wavelet, and b is a parameter defining the location of the wavelet. At step 36, a first derivative of the continuous wavelet transform is calculated. This step allows to identify heel-strike events as the minima of the first derivative. At optional step 38, a second derivative of the continuous wavelet transform is calculated. This step allows to identify toe-off events as the maxima of the second derivative. In another embodiment, toe-off events are the minima of the first derivative and heel-strike events are the maxima of the second derivative. At step 40, one or more gait features can be extracted. For example, gait features such as the timing and/or location of the heel-strike events, and/or of the toe-off events can be extracted. Other gait features can be extracted from the heel-strike events and optionally the toe-off events, such as for example cadence, fatigue, stability, rhythm/variability, asymmetry, pace, forward balance, lateral balance. Step 40 can further comprise a refinement of the gait feature extraction. For example, false positive (heel-strike or toe-off) events can be removed. This can be done by setting predetermined thresholds, for example on the stride duration.

Figure 4:
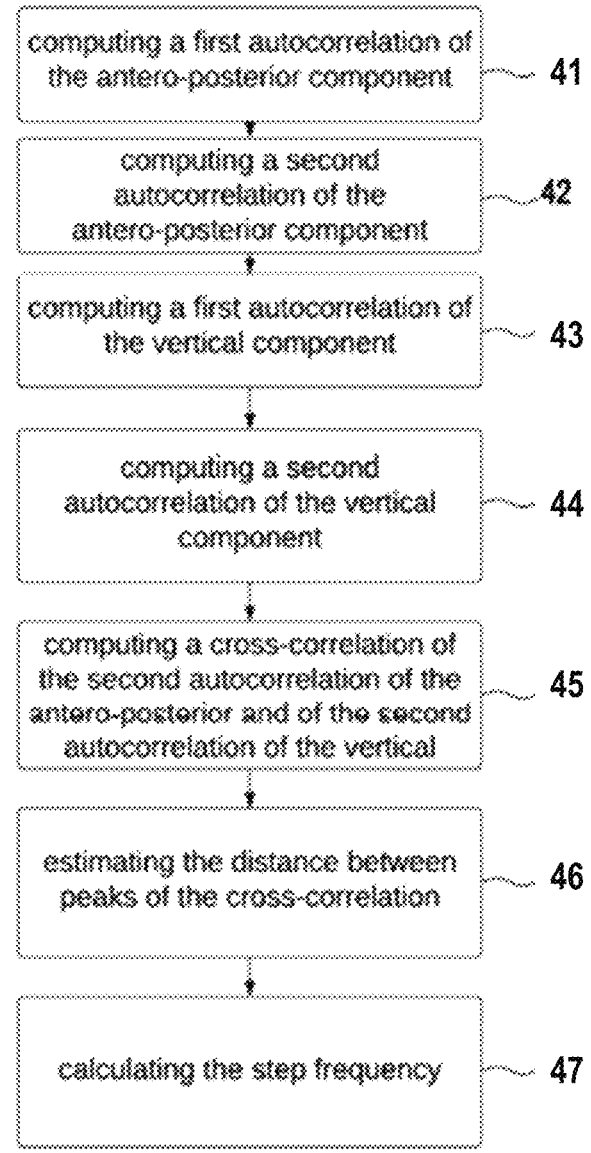
FIG. 4 is a flow diagram showing, in schematic form, an example of a method of calculating the step frequency of a subject, according to some example embodiments.

FIG. 4 is a flow diagram showing, in schematic form, a method of calculating the step frequency of a subject, according to some example embodiments. This method can be performed after the method of FIG. 2D. This method can implement step 30 of FIG. 3. With reference to FIG. 4, at step 41 a first autocorrelation of the antero-posterior component is computed (auto$_{AP}$). At step 42, a second autocorrelation of the antero-posterior component is computed (auto2$_{AP}$). The second autocorrelation is computed as the autocorrelation between the first autocorrelation of the antero-posterior component and a time-shifted version of the first autocorrelation of the antero-posterior component (auto2$_{AP}$=autocorrelation(auto$_{AP}$, auto$_{AP}$(t)), where auto$_{AP}$(t) is a time-shifted version of auto$_{AP}$). At step 43, a first autocorrelation of the vertical component is computed (auto$_V$). At step 44, a second autocorrelation of the vertical component is computed (auto2$_V$). The second autocorrelation is computed as the autocorrelation between the first autocorrelation of the vertical component and a time-shifted version of the first autocorrelation of the vertical component (auto2$_V$=autocorrelation(auto$_V$, auto$_V$(t)), where auto$_V$(t) is a time-shifted version of auto$_V$). Steps 43 and 44 can be performed before steps 41 and 42. At step 45, a cross-correlation of the second autocorrelation of the antero-posterior component and of the second autocorrelation of the vertical component is computed. At step 46, the distance between peaks of the cross-correlation is estimated. The distance between every other peak contains information about the stride duration. The stride duration can be computed via a summarized metric of the distance between every other peak. Said summarized metric can comprise mean, median, trimmed versions thereof. The distance between every peak contains information about the step duration. The step duration can be computed via a summa-rized metric of the distance between every peak. Said summarized metric can comprise mean, median, trimmed versions thereof. At step 47, the step frequency is calculated from the estimated distance between peaks. In an embodiment, the step frequency is calculated as the half of the inverse of the stride duration. In another embodiment, the step frequency is calculated as the inverse of the step duration. The step frequency calculated from the stride duration and the step frequency calculated from the step duration shall lead to a similar result within a certain precision. In another embodiment, the antero-posterior component is replaced by the medio-lateral component. This can be useful for example when analyzing signals from a U-Turn test.

FIG. 5 is a flow diagram showing, in schematic form, a method of selecting the wavelet axis of a continuous wavelet function, according to some example embodiments. This method can be performed after the method of FIG. 2D. This method can implement step 34 of FIG. 3. With reference to FIG. 5, at step 50 a power spectral density for each autocorrelation of the directional components is calculated. A general mathematical expression of a power spectral density is the following (Equation 5):

$$PSD(f) = \lim_{T \to \infty} \frac{1}{T} |\hat{x}_T(f)|^2$$

where t is the time, T is a time period, $\hat{x}_T(f)$ is the Fourier transform of $x_T(t)=x(t)\omega_T(t)$, where x(t) is the autocorrelation of a directional component and $\omega_T(t)$ is a function equal to 1 within the time period T and 0 elsewhere.

At step 52, an interval is selected comprising the calculated step frequency. The interval is a frequency (or power) interval. The interval can be defined as a range of values within +/−25% (or within +/−10%, +/−15%, +/−25%, or +/−30%) of the calculated step frequency, such as e.g. values at or above S−0.25S and at or below S+0.25S, where S is the step frequency. At step 54, the directional component with the highest power spectral density in the selected interval is selected. At step 56, the selected directional component is identified as the wavelet axis. The wavelet axis defines which directional component of the signal undergoes the continuous wavelet transform.

FIG. 6 is a flow diagram showing, in schematic form, a method of estimating the wavelet sign of a continuous wavelet function, according to some example embodiments. This method can be performed after the method of FIG. 2D. This method can implement step 34 of FIG. 2D. With reference to FIG. 6, at step 60, a norm of the accelerometer signal block is computed (|acc|). At step 62, a correlation of the parameterized continuous wavelet function and of the calculated norm is computed. In an embodiment the correlation is computed via a Pearson coefficient. At step 64, the wavelet sign is determined. The wavelet sign can be determined based on the sign of the computed cross-correlation. If the sign of the computed correlation is positive, then the wavelet sign is positive. If the sign of the computed correlation is negative, then the wavelet sign is negative. In an embodiment, if the correlation is zero, then the correlation of the norm of the accelerometer signal block and of the medio-lateral gyroscope signal block can be computed. If the latter correlation is negative, the wavelet sign is positive. If the latter correlation is positive, the wavelet sign is negative. Step 62 can comprise a filtering of the antero-posterior component. For example, the signals can be filtered using a 2$^{nd}$ order Butterworth low-pass filter. The filter can have a cut-off frequency to select the low-frequency spectrum, wherein harmonic frequencies related to gait activity mainly appear. A suitable cut-off frequency can be 2 Hz. Step 62 can comprise a filtering of the correlation. If the correlation is below a predetermined minimum threshold, the correlation is truncated to zero. Experimental results show that said predetermined minimum threshold can be below 0.3.

FIG. 7 is a summary figure showing the methods of the previous figures relative to each other, according to some example embodiments. At step 70, signals are processed to identify horizontal components according to FIG. 2D. At step 72, a step frequency is calculated according to FIG. 4. At step 74, one or more gait features are extracted according to FIG. 3 using a wavelet transform characterized using methods of FIGS. 5-6.

EXAMPLES

The examples below illustrate some applications of the present disclosure, in particular in the context of analyzing signals associated with gait activity of a subject for the purposes of assessing symptoms of MS.

The signals processed and analyzed in the following examples were received from subjects undergoing several tests in two on-site visits in a gait laboratory and during an unsupervised remote testing period for 10-14 days in between the on-site visits. The participants performed several gait and balance tests, including a 2MWT (2-Minute-Walking-Test), a U-Turn Test, and a SBT (Static Balance Test). The 2MWT comprised four separate conditions, or walking tasks, each lasting two minutes: 1) fixed speed (2 km/h), 2) self-paced (at normal pace), 3) fast-paced (as fast as the subject can walk safely), and 4) dual-task (self-paced condition with a simultaneous cognitive task consisting of serial subtractions of 7 starting from 200). The U-Turn Test instructed the participants to walk back and forth for 60 seconds while performing U-turns roughly 3 or 4 m apart. The SBT battery consisted of five test conditions, each performed twice and lasting 30 seconds: 1) natural stance with feet apart and eyes open, 2) natural stance with feet apart and eyes closed, 3) parallel stance with feet together and eyes open, 4) full tandem stance with eyes open, 5) single foot stance with eyes open. The participants carried smartphones in six different locations: right and left front pockets, central front at the waist, left and right back pockets, back waist.

Figure 8A:
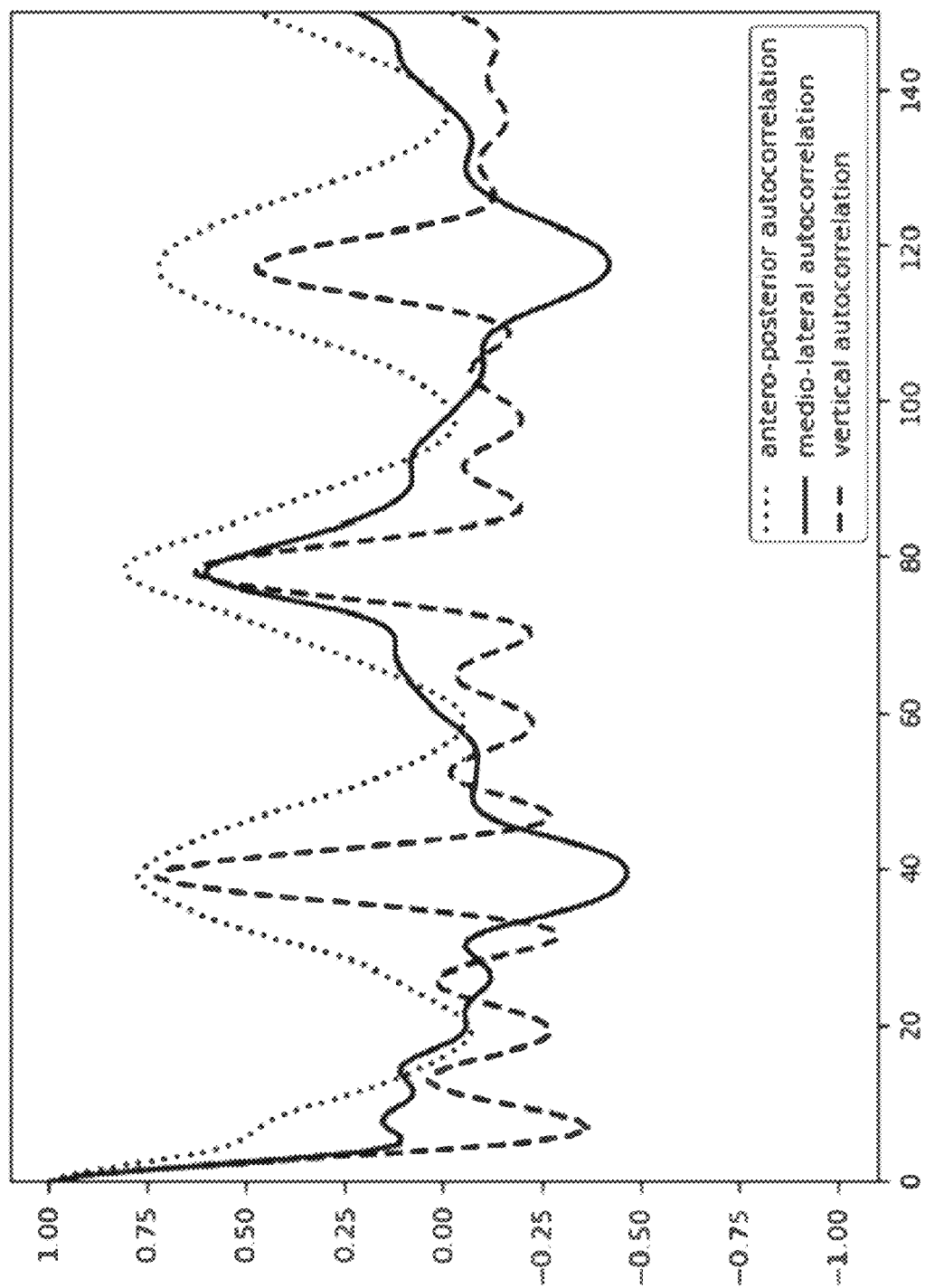
FIG. 8A shows an example of the autocorrelations of the three-dimensional components of signals selected in a straight-gait block obtained from a wearable motion sensor on a subject, according to some example embodiments.

FIGS. 8A-B show an example of a method of processing signals from one wearable motion sensor to analyze gait activity of a subject, according to some example embodiments. The signals received were divided in signal blocks and resampled to a sampling frequency of 50 Hz, e.g., each sample duration was 0.02 seconds. The three directional components, e.g., vertical, antero-posterior, and medio-lateral, were obtained by applying a Madgwick filter to the 3D signals and a PCA. FIG. 8A shows the autocorrelations of the three directional components, e.g., antero-posterior, medio-lateral and vertical components, of the signals selected in a straight-gait block obtained from a wearable sensor on a subject. FIG. 8B shows the sum of the three autocorrelations, the norm of the three autocorrelations, and the autocorrelation of the summed sum and norm. The first peak of the autocorrelation of the summed curves, marked by a vertical line, was used to estimate the step duration. In this example, the estimation of the step duration was slightly below 40 samples, e.g., 0.8 seconds. The estimated step duration was used to validate the directional component curves according to the present disclosure, namely: the peak located at around 40 samples in the antero-posterior component was positive and the peak located at around 40 samples in the medio-lateral component was negative, thus confirming that the antero-posterior component and the medio-lateral components were correct as identified through the Madgwick filter and PCA. In the literature, the three directional components are obtained by projecting the signals on the global walking directions assumed by a predefined frame of reference. With the computer-implemented method of the present disclosure as hereinbefore described, the directional components may be estimated and the estimated directional components may be confirmed without the need for assuming a predefined frame of reference.

Figure 9A:
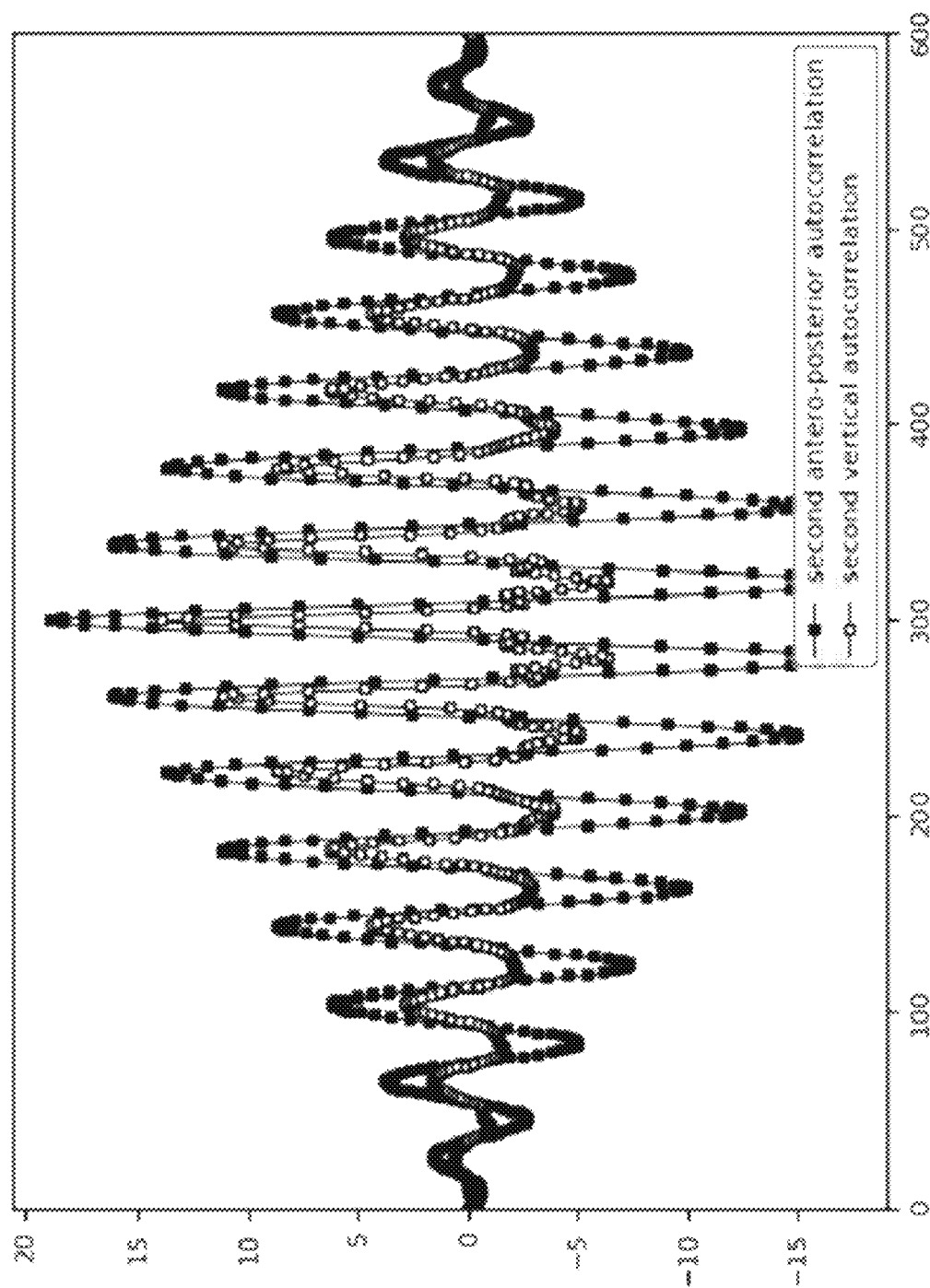
FIG. 9A shows an example of the second autocorrelations of two directional components, according to some example embodiments.

FIGS. 9A-B show an example of a method of calculating the step frequency of a subject, according to some example embodiments. FIG. 9A shows the second autocorrelations of two directional components, in particular the antero-posterior and vertical components. FIG. 9B shows the cross-correlation of the two curves in FIG. 9A. Starting from the first peak at around 40 samples, every other peak is marked by a vertical line. The distance between the vertical lines quantifies the stride duration. An aggregate estimate of the stride duration was obtained by calculating the median of the distances between the vertical lines, e.g., between every other peak. A peak-finding function, e.g., a function that takes in input the stride duration and outputs the position of the peaks, was used to find the peaks in the cross-correlation curve. In this example, a further validation step was performed at this point: it was verified that a peak existed at a location of roughly half of the stride duration in the auto-correlation of the directional components. If this was the case, then the stride duration estimated was considered reliable, otherwise the peak-finding function was recalculated with an updated input, for example the stride duration increased by 0.02 seconds, until the new stride duration could be considered reliable. The estimated step frequency was then calculated as half the inverse of the stride duration. In this example, the estimated stride duration was circa 80 samples (1.6 seconds), and the estimated step frequency was 1.25 Hz. In the literature, a step frequency is estimated directly from the peaks of the autocorrelations. However, such method is not robust enough in comparing signals from different patients or different sensor locations and/or orientations. Accordingly, various embodiments of the present disclosure leverage more robust estimation of the step frequency to extract gait features comparable across subjects. Furthermore, various embodiments of the present disclosure also apply more robust estimation of the step frequency to extract gait features comparable across sensor locations and/or orientations. Additionally, in the literature the wavelet scale of the continuous wavelet function used for analyzing the signals is either set as a constant (McCamley et al, 2012; Godfrey et al, 2014; Del Din et al, 2015) or set as proportional to a constant step frequency (Ning et al, 2019; Zhou et al, 2016), or chosen via a regression model (Caramia et al, 2019) or as the most dominant frequency of the power spectral density (Pham et al, 2017). More robust estimation of the step frequency may also be used, according to various embodiments of the present disclosure, to precisely calculate the wavelet scale of the continuous wavelet function, which in turns results in more accurate gait features.

Embodiments

The specific embodiments described herein are offered by way of example, not by way of limitation. Various modifications and variations of the described compositions, methods, and uses of the technology will be apparent to those skilled in the art without departing from the scope and spirit of the technology as described. Any sub-titles herein are included for convenience only, and are not to be construed as limiting the disclosure in any way.

The methods of any embodiments described herein may be provided as computer programs or as computer program products or computer readable media carrying a computer program which is arranged, when run on a computer, to perform the method(s) described above.

Unless context dictates otherwise, the descriptions and definitions of the features set out above are not limited to any particular aspect or embodiment of the present disclosure and apply equally to all aspects and embodiments which are described.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the present disclosure may be readily combined, without departing from the scope or spirit of the present disclosure.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the present disclosure provide the aspects and embodiments described above with the term "comprising" replaced by the term "consisting of" or "consisting essentially of", unless the context dictates otherwise.

The features disclosed in the description, or in the following claims, or in the accompanying drawings, expressed in their specific forms or in terms of a means for performing the disclosed function, or a method or process for obtaining the disclosed results, as appropriate, may, separately, or in any combination of such features, be utilized for realizing the present disclosure in diverse forms thereof.

1. In an embodiment, a computer-implemented method of processing signals from one or more wearable motion sensors to analyze gait activity of a subject is disclosed, the method comprising the steps of:
   a. receiving signals from the one or more wearable motion sensors located in any orientation on the subject, wherein the one or more wearable motion sensors comprise an accelerometer and a gyroscope; and
   b. processing the received signals, wherein processing comprises:
      i. dividing the signals from each sensor into a plurality of signal blocks comprising the signal of the respective sensor over a time interval;
      ii. determining, for at least one of the plurality of signal blocks, directional components of the signal block, wherein determining directional components comprises:
         a. determining a vertical component of the signal block along the direction of gravity;
         b. estimating horizontal components of the signal block in the plane perpendicular to the direction of gravity, wherein the horizontal components consist of an antero-posterior component and a medio-lateral component;
         c. computing an autocorrelation of the vertical component of the signal block;
         d. computing an autocorrelation of each estimated horizontal component of the signal block;
         e. calculating the sum of the autocorrelations of each horizontal component obtained in step d. and of the autocorrelation of the vertical component obtained in step c.;
         f. calculating the norm of the autocorrelations of each horizontal component obtained in step d. and of the autocorrelation of the vertical component obtained in step c.;
         g. calculating the sum of the sum of autocorrelations obtained in step e. and of the norm of autocorrelations obtained in step f.;
         h. computing an autocorrelation of the sum calculated in step g.;
         i. estimating the location of the first peak of the autocorrelation obtained in step h.;
         j. selecting, in each autocorrelation of the horizontal components, the peak located at the location of the first peak estimated in step i.;
         k. validating the horizontal components of the signal block using one or more predetermined criteria that apply to the signs of the selected peaks of each autocorrelation of the horizontal components.

2. In an embodiment, a computer-implemented method of processing signals from one or more wearable motion sensors is disclosed, the method comprising the steps of:
   a. receiving signals from the one or more wearable motion sensors located in any orientation on the subject, wherein the one or more wearable motion sensors comprise an accelerometer and a gyroscope; and
   b. processing the received signals, wherein processing comprises:
      i. dividing the signals from each sensor into a plurality of signal blocks comprising the signal of the respective sensor over a time interval;
      ii. determining, for at least one of the plurality of signal blocks, directional components of the signal block, wherein determining directional components comprises:

a. determining a vertical component of the signal block along the direction of gravity;
b. estimating horizontal components of the signal block in the plane perpendicular to the direction of gravity, wherein the horizontal components consist of an antero-posterior component and a medio-lateral component;
c. computing an autocorrelation of the vertical component of the signal block;
d. computing an autocorrelation of each estimated horizontal component of the signal block;
e. calculating the sum of the autocorrelations of each horizontal component obtained in step d. and of the autocorrelation of the vertical component obtained in step c.;
f. calculating the norm of the autocorrelations of each horizontal component obtained in step d. and of the autocorrelation of the vertical component obtained in step c.;
g. calculating the sum of the sum of autocorrelations obtained in step e. and of the norm of autocorrelations obtained in step f.;
h. computing an autocorrelation of the sum calculated in step g.;
i. estimating the location of the first peak of the autocorrelation obtained in step h.;
j. selecting, in each autocorrelation of the horizontal components, the peak located at the location of the first peak estimated in step i.;
k. validating the horizontal components of the signal block using one or more predetermined criteria that apply to the signs of the selected peaks of each autocorrelation of the horizontal components.

3. In an embodiment, a computer-implemented method of processing signals from one or more wearable motion sensors to analyze gait activity of a subject is disclosed, the method comprising the steps of:
a. receiving signals from the one or more wearable motion sensors located in any orientation on the subject; and
b. processing the received signals, wherein processing comprises:
   i. dividing the signals from each sensor into a plurality of signal blocks comprising the signal of the respective sensor over a time interval;
   ii. determining, for at least one of the plurality of signal blocks, directional components of the signal block, wherein determining directional components comprises:
      a. determining a vertical component of the signal block along the direction of gravity;
      b. estimating horizontal components of the signal block in the plane perpendicular to the direction of gravity, wherein the horizontal components consist of an antero-posterior component and a medio-lateral component;
      c. computing an autocorrelation of the vertical component of the signal block;
      d. computing an autocorrelation of each estimated horizontal component of the signal block;
      e. calculating the sum of the autocorrelations of each horizontal component obtained in step d. and of the autocorrelation of the vertical component obtained in step c.;
      f. calculating the norm of the autocorrelations of each horizontal component obtained in step d. and of the autocorrelation of the vertical component obtained in step c.;
      g. calculating the sum of the sum of autocorrelations obtained in step e. and of the norm of autocorrelations obtained in step f.;
      h. computing an autocorrelation of the sum calculated in step g.;
      i. estimating the location of the first peak of the autocorrelation obtained in step h.;
      j. selecting, in each autocorrelation of the horizontal components, the peak located at the location of the first peak estimated in step i.;
      k. validating the horizontal components of the signal block using one or more predetermined criteria that apply to the signs of the selected peaks of each autocorrelation of the horizontal components.

4. In an embodiment, a computer-implemented method of processing signals from one or more wearable motion sensors is disclosed, the method comprising the steps of:
a. receiving signals from the one or more wearable motion sensors located in any orientation on the subject; and
b. processing the received signals, wherein processing comprises:
   i. dividing the signals from each sensor into a plurality of signal blocks comprising the signal of the respective sensor over a time interval;
   ii. determining, for at least one of the plurality of signal blocks, directional components of the signal block, wherein determining directional components comprises:
      a. determining a vertical component of the signal block along the direction of gravity;
      b. estimating horizontal components of the signal block in the plane perpendicular to the direction of gravity, wherein the horizontal components consist of an antero-posterior component and a medio-lateral component;
      c. computing an autocorrelation of the vertical component of the signal block;
      d. computing an autocorrelation of each estimated horizontal component of the signal block;
      e. calculating the sum of the autocorrelations of each horizontal component obtained in step d. and of the autocorrelation of the vertical component obtained in step c.;
      f. calculating the norm of the autocorrelations of each horizontal component obtained in step d. and of the autocorrelation of the vertical component obtained in step c.;
      g. calculating the sum of the sum of autocorrelations obtained in step e. and of the norm of autocorrelations obtained in step f.;
      h. computing an autocorrelation of the sum calculated in step g.;
      i. estimating the location of the first peak of the autocorrelation obtained in step h.;
      j. selecting, in each autocorrelation of the horizontal components, the peak located at the location of the first peak estimated in step i.;
      k. validating the horizontal components of the signal block using one or more predetermined criteria that apply to the signs of the selected peaks of each autocorrelation of the horizontal components.

5. In an embodiment, the method of any preceding embodiments is disclosed, wherein processing the received signals further comprises:
   a. classifying one or more of the plurality of signal blocks between a plurality of categories comprising at least a rest category and a non-rest category, the non-rest category comprising at least a straight-gait category, using the magnitude and/or standard deviation of the respective signal block;
   b. selecting one or more of a plurality of signal blocks classified as at least one of the plurality of categories; and wherein the step of determining directional components is performed on one or more of the selected signal blocks.
6. In an embodiment, the method of any preceding embodiments is disclosed, wherein processing the received signals further comprises:
   a. classifying one or more of the plurality of signal blocks between a plurality of categories comprising at least a rest category and a non-rest category, the non-rest category comprising at least a straight-gait category, using the magnitude and/or standard deviation of the respective signal block;
   b. selecting one or more of a plurality of signal blocks classified as at least one of the plurality of categories;
7. In an embodiment, a computer-implemented method of processing signals from one or more wearable motion sensors to analyze gait activity of a subject is disclosed, the method comprising the steps of:
   a. receiving signals from the one or more wearable motion sensors located in any orientation on the subject, wherein the one or more wearable motion sensors comprise an accelerometer and a gyroscope; and
   b. processing the received signals, wherein processing comprises:
      i. dividing the signals from each sensor into a plurality of signal blocks comprising the signal of the respective sensor over a time interval;
      ii. classifying one or more of the plurality of signal blocks between a plurality of categories comprising at least a rest category and a non-rest category, the non-rest category comprising at least a straight-gait category, using the magnitude and/or standard deviation of the respective signal block;
      iii. selecting one or more of a plurality of signal blocks classified as at least one of the plurality of categories;
      iv. determining, for at least one of the selected one or more signal blocks, directional components of the signal block, wherein determining directional components comprises:
         a. determining a vertical component of the signal block along the direction of gravity;
         b. estimating horizontal components of the signal block in the plane perpendicular to the direction of gravity, wherein the horizontal components consist of an antero-posterior component and a medio-lateral component;
         c. computing an autocorrelation of the vertical component of the signal block;
         d. computing an autocorrelation of each estimated horizontal component of the signal block;
         e. calculating the sum of the autocorrelations of each horizontal component obtained in step d. and of the autocorrelation of the vertical component obtained in step c.;
         f. calculating the norm of the autocorrelations of each horizontal component obtained in step d. and of the autocorrelation of the vertical component obtained in step c.;
         g. calculating the sum of the sum of autocorrelations obtained in step e. and of the norm of autocorrelations obtained in step f.;
         h. computing an autocorrelation of the sum calculated in step g.;
         i. estimating the location of the first peak of the autocorrelation obtained in step h.;
         j. selecting, in each autocorrelation of the horizontal components, the peak located at the location of the first peak estimated in step i.;
         k. validating the horizontal components of the signal block using one or more predetermined criteria that apply to the signs of the selected peaks of each autocorrelation of the horizontal components.
8. In an embodiment, a computer-implemented method of processing signals from one or more wearable motion sensors is disclosed, the method comprising the steps of:
   a. receiving signals from the one or more wearable motion sensors located in any orientation on the subject, wherein the one or more wearable motion sensors comprise an accelerometer and a gyroscope; and
   b. processing the received signals, wherein processing comprises:
      i. dividing the signals from each sensor into a plurality of signal blocks comprising the signal of the respective sensor over a time interval;
      ii. classifying one or more of the plurality of signal blocks between a plurality of categories comprising at least a rest category and a non-rest category, the non-rest category comprising at least a straight-gait category, using the magnitude and/or standard deviation of the respective signal block;
      iii. selecting one or more of a plurality of signal blocks classified as at least one of the plurality of categories;
      iv. determining, for at least one of the selected one or more signal blocks, directional components of the signal block, wherein determining directional components comprises:
         a. determining a vertical component of the signal block along the direction of gravity;
         b. estimating horizontal components of the signal block in the plane perpendicular to the direction of gravity, wherein the horizontal components consist of an antero-posterior component and a medio-lateral component;
         c. computing an autocorrelation of the vertical component of the signal block;
         d. computing an autocorrelation of each estimated horizontal component of the signal block;
         e. calculating the sum of the autocorrelations of each horizontal component obtained in step d. and of the autocorrelation of the vertical component obtained in step c.;
         f. calculating the norm of the autocorrelations of each horizontal component obtained in step d. and of the autocorrelation of the vertical component obtained in step c.;

g. calculating the sum of the sum of autocorrelations obtained in step e. and of the norm of autocorrelations obtained in step f.;
h. computing an autocorrelation of the sum calculated in step g.;
i. estimating the location of the first peak of the autocorrelation obtained in step h.;
j. selecting, in each autocorrelation of the horizontal components, the peak located at the location of the first peak estimated in step i.;
k. validating the horizontal components of the signal block using one or more predetermined criteria that apply to the signs of the selected peaks of each autocorrelation of the horizontal components.

9. In an embodiment, a computer-implemented method of processing signals from one or more wearable motion sensors to analyze gait activity of a subject is disclosed, the method comprising the steps of:
a. receiving signals from the one or more wearable motion sensors located in any orientation on the subject, wherein the one or more wearable motion sensors comprise an accelerometer and a gyroscope; and
b. processing the received signals, wherein processing comprises determining directional components of the received signals, wherein determining directional components comprises:
   a. determining a vertical component of the signal along the direction of gravity;
   b. estimating horizontal components of the signal in the plane perpendicular to the direction of gravity, wherein the horizontal components consist of an antero-posterior component and a medio-lateral component;
   c. computing an autocorrelation of the vertical component of the signal;
   d. computing an autocorrelation of each estimated horizontal component of the signal;
   e. calculating the sum of the autocorrelations of each horizontal component obtained in step d. and of the autocorrelation of the vertical component obtained in step c.;
   f. calculating the norm of the autocorrelations of each horizontal component obtained in step d. and of the autocorrelation of the vertical component obtained in step c.;
   g. calculating the sum of the sum of autocorrelations obtained in step e. and of the norm of autocorrelations obtained in step f.;
   h. computing an autocorrelation of the sum calculated in step g.;
   i. estimating the location of the first peak of the autocorrelation obtained in step h.;
   j. selecting, in each autocorrelation of the horizontal components, the peak located at the location of the first peak estimated in step i.;
   k. validating the horizontal components of the signal using one or more predetermined criteria that apply to the signs of the selected peaks of each autocorrelation of the horizontal components.

10. In an embodiment, a computer-implemented method of processing signals from one or more wearable motion sensors is disclosed, the method comprising the steps of:
a. receiving signals from the one or more wearable motion sensors located in any orientation on the subject, wherein the one or more wearable motion sensors comprise an accelerometer and a gyroscope; and
b. processing the received signals, wherein processing comprises determining directional components of the received signals, wherein determining directional components comprises:
   a. determining a vertical component of the signal along the direction of gravity;
   b. estimating horizontal components of the signal in the plane perpendicular to the direction of gravity, wherein the horizontal components consist of an antero-posterior component and a medio-lateral component;
   c. computing an autocorrelation of the vertical component of the signal;
   d. computing an autocorrelation of each estimated horizontal component of the signal;
   e. calculating the sum of the autocorrelations of each horizontal component obtained in step d. and of the autocorrelation of the vertical component obtained in step c.;
   f. calculating the norm of the autocorrelations of each horizontal component obtained in step d. and of the autocorrelation of the vertical component obtained in step c.;
   g. calculating the sum of the sum of autocorrelations obtained in step e. and of the norm of autocorrelations obtained in step f.;
   h. computing an autocorrelation of the sum calculated in step g.;
   i. estimating the location of the first peak of the autocorrelation obtained in step h.;
   j. selecting, in each autocorrelation of the horizontal components, the peak located at the location of the first peak estimated in step i.;
   k. validating the horizontal components of the signal using one or more predetermined criteria that apply to the signs of the selected peaks of each autocorrelation of the horizontal components.

11. In an embodiment, a computer-implemented method of processing signals from one or more wearable motion sensors to analyze gait activity of a subject is disclosed, the method comprising the steps of:
a. receiving signals from the one or more wearable motion sensors located in any orientation on the subject, wherein the one or more wearable motion sensors comprise an accelerometer and a gyroscope; and
b. processing the received signals, wherein processing comprises:
   i. dividing the signals from at least one sensor into a plurality of signal blocks comprising the signal of the respective sensor over a time interval;
   ii. classifying one or more of the plurality of signal blocks between a plurality of categories comprising at least a rest category and a non-rest category, using the magnitude and/or standard deviation of the respective signal block;
   iii. selecting one or more of a plurality of signal blocks classified as at least one of the plurality of categories;
   iv. determining, for at least one of the selected one or more signal blocks, directional components of the signal block, wherein determining directional components comprises:

a. determining a vertical component of the signal block along the direction of gravity;
b. estimating horizontal components of the signal block in the plane perpendicular to the direction of gravity, wherein the horizontal components consist of an antero-posterior component and a medio-lateral component;
c. computing an autocorrelation of the vertical component of the signal block;
d. computing an autocorrelation of each estimated horizontal component of the signal block;
e. calculating the sum of the autocorrelations of each horizontal component obtained in step d. and of the autocorrelation of the vertical component obtained in step c.;
f. calculating the norm of the autocorrelations of each horizontal component obtained in step d. and of the autocorrelation of the vertical component obtained in step c.;
g. calculating the sum of the sum of autocorrelations obtained in step e. and of the norm of autocorrelations obtained in step f.;
h. computing an autocorrelation of the sum calculated in step g.;
i. estimating the location of the first peak of the autocorrelation obtained in step h.;
j. selecting, in each autocorrelation of the horizontal components, the peak located at the location of the first peak estimated in step i.;
k. validating the horizontal components of the signal block using one or more predetermined criteria that apply to the signs of the selected peaks of each autocorrelation of the horizontal components.

12. In an embodiment, a computer-implemented method of processing signals from one or more wearable motion sensors to analyze gait activity of a subject is disclosed, the method comprising the steps of:
a. receiving signals from the one or more wearable motion sensors located in any orientation on the subject, wherein the one or more wearable motion sensors comprise an accelerometer and a gyroscope; and
b. processing the received signals, wherein processing comprises:
i. dividing the signals from each sensor into a plurality of signal blocks comprising the signal of the respective sensor over a time interval;
ii. classifying one or more of the plurality of signal blocks between a plurality of categories comprising at least a rest category and a non-rest category, the non-rest category comprising at least a straight-gait category, using the magnitude and standard deviation of the respective signal block;
iii. selecting one or more of a plurality of signal blocks classified as at least one of the plurality of categories;
iv. determining, for at least one of the selected one or more signal blocks, directional components of the signal block, wherein determining directional components comprises:
a. determining a vertical component of the signal block along the direction of gravity;
b. estimating horizontal components of the signal block in the plane perpendicular to the direction of gravity, wherein the horizontal components consist of an antero-posterior component and a medio-lateral component;
c. computing an autocorrelation of the vertical component of the signal block;
d. computing an autocorrelation of each estimated horizontal component of the signal block;
e. calculating the sum of the autocorrelations of each horizontal component obtained in step d. and of the autocorrelation of the vertical component obtained in step c.;
f. calculating the norm of the autocorrelations of each horizontal component obtained in step d. and of the autocorrelation of the vertical component obtained in step c.;
g. calculating the sum of the sum of autocorrelations obtained in step e. and of the norm of autocorrelations obtained in step f.;
h. computing an autocorrelation of the sum calculated in step g.;
i. estimating the location of the first peak of the autocorrelation obtained in step h.;
j. selecting, in each autocorrelation of the horizontal components, the peak located at the location of the first peak estimated in step i.;
k. validating the horizontal components of the signal block using one or more predetermined criteria that apply to the signs of the selected peaks of each autocorrelation of the horizontal components.

13. In an embodiment, a computer-implemented method of processing signals from one or more wearable motion sensors to analyze gait activity of a subject is disclosed, the method comprising the steps of:
a. receiving signals from the one or more wearable motion sensors located in any orientation on the subject, wherein the one or more wearable motion sensors comprise an accelerometer and a gyroscope; and
b. processing the received signals, wherein processing comprises:
i. dividing the signals from each sensor into a plurality of signal blocks comprising the signal of the respective sensor over a time interval;
ii. classifying one or more of the plurality of signal blocks between a plurality of categories comprising at least a rest category and a non-rest category, the non-rest category comprising at least a straight-gait category, using the magnitude or standard deviation of the respective signal block;
iii. selecting one or more of a plurality of signal blocks classified as at least one of the plurality of categories;
iv. determining, for at least one of the selected one or more signal blocks, directional components of the signal block, wherein determining directional components comprises:
a. determining a vertical component of the signal block along the direction of gravity;
b. estimating horizontal components of the signal block in the plane perpendicular to the direction of gravity, wherein the horizontal components consist of an antero-posterior component and a medio-lateral component;
c. computing an autocorrelation of the vertical component of the signal block;
d. computing an autocorrelation of each estimated horizontal component of the signal block;

e. calculating the sum of the autocorrelations of each horizontal component obtained in step d. and of the autocorrelation of the vertical component obtained in step c.;

f. calculating the norm of the autocorrelations of each horizontal component obtained in step d. and of the autocorrelation of the vertical component obtained in step c.;

g. calculating the sum of the sum of autocorrelations obtained in step e. and of the norm of autocorrelations obtained in step f.;

h. computing an autocorrelation of the sum calculated in step g.;

i. estimating the location of the first peak of the autocorrelation obtained in step h.;

j. selecting, in each autocorrelation of the horizontal components, the peak located at the location of the first peak estimated in step i.;

k. validating the horizontal components of the signal block using one or more predetermined criteria that apply to the signs of the selected peaks of each autocorrelation of the horizontal components.

14. In an embodiment, the method of any preceding embodiments is disclosed, wherein the steps are performed in different order.

15. In an embodiment, the method of any preceding embodiments is disclosed, wherein the processing is performed independently using signals from an accelerometer.

16. In an embodiment, the method of any preceding embodiments is disclosed, wherein the processing is performed independently using signals from a gyroscope.

17. In an embodiment, the method of any preceding embodiments is disclosed, wherein validating the horizontal components of the signal block using one or more predetermined criteria that apply to the signs of the selected peaks of each autocorrelation of the horizontal components comprises:

a. determining, based on the results of evaluation of the one or more predetermined criteria, that the estimated horizontal components are correctly identified, and/or b. determining, based on the results of evaluation of the one or more predetermined criteria, that the estimated horizontal components are incorrectly identified.

18. In an embodiment, the method of any preceding embodiments is disclosed, wherein validating the horizontal components of the signal block using one or more predetermined criteria that apply to the signs of the selected peaks of each autocorrelation of the horizontal components comprises:

a. determining, based on the results of evaluation of the one or more predetermined criteria, that the estimated horizontal components are correctly identified, and b. determining, based on the results of evaluation of the one or more predetermined criteria, that the estimated horizontal components are incorrectly identified.

19. In an embodiment, the method of any preceding embodiments is disclosed, wherein validating the horizontal components of the signal block using one or more predetermined criteria that apply to the signs of the selected peaks of each autocorrelation of the horizontal components comprises:

a. determining, based on the results of evaluation of the one or more predetermined criteria, that the estimated horizontal components are correctly identified, or b. determining, based on the results of evaluation of the one or more predetermined criteria, that the estimated horizontal components are incorrectly identified.

20. In an embodiment, the method of any preceding embodiments is disclosed, wherein dividing the signals from each sensor into a plurality of signal blocks comprising the signal of the respective sensor over a time interval comprises dividing the signals from each sensor into a plurality of non-overlapping signal blocks and/or a plurality of signal blocks of a predetermined duration.

21. In an embodiment, the method of any preceding embodiments is disclosed, wherein dividing the signals from each sensor into a plurality of signal blocks comprising the signal of the respective sensor over a time interval comprises dividing the signals from each sensor into a plurality of non-overlapping signal blocks and a plurality of signal blocks of a predetermined duration.

22. In an embodiment, the method of any preceding embodiments is disclosed, wherein dividing the signals from each sensor into a plurality of signal blocks comprising the signal of the respective sensor over a time interval comprises dividing the signals from each sensor into a plurality of non-overlapping signal blocks or a plurality of signal blocks of a predetermined duration.

23. In an embodiment, the method of any preceding embodiments is disclosed, wherein the rest category comprises a short-rest category and a long-rest category, based on a predetermined rest duration threshold.

24. In an embodiment, the method of any preceding embodiments is disclosed, wherein the straight-gait category comprises signal blocks with gyroscope signal magnitude below a predetermined minimum threshold.

25. In an embodiment, the method of any preceding embodiments is disclosed, further comprising, for at least one of the plurality of signal blocks, the steps of:
a. calculating, using the determined directional components of the signal block, a step frequency;
b. selecting one of the determined directional components of the signal block using the calculated step frequency and the computed autocorrelations of each directional component;
c. obtaining a continuous wavelet transform of the selected directional component;
d. calculating at least a first derivative of the continuous wavelet transform, and optionally a second derivative of the continuous wavelet transform;
e. extracting, from the calculated at least first derivative and optionally second derivative of the continuous wavelet transform, one or more gait features.

26. In an embodiment, the method of any preceding embodiments is disclosed, further comprising, for at least one of the plurality of signal blocks, the steps of:
a. calculating, using the determined directional components of the signal block, a step frequency;

b. selecting one of the determined directional components of the signal block using the calculated step frequency and the computed autocorrelations of each directional component;
c. obtaining a continuous wavelet transform of the selected directional component;
d. calculating at least a first derivative of the continuous wavelet transform;
e. extracting, from the calculated at least first derivative, one or more gait features.

27. In an embodiment, the method of any preceding embodiments is disclosed, further comprising, for each one of the plurality of signal blocks, the steps of:
a. calculating, using the determined directional components of the signal block, a step frequency;
b. selecting one of the determined directional components of the signal block using the calculated step frequency and the computed autocorrelations of each directional component;
c. obtaining a continuous wavelet transform of the selected directional component;
d. calculating at least a first derivative of the continuous wavelet transform, and optionally a second derivative of the continuous wavelet transform;
e. extracting, from the calculated at least first derivative and optionally second derivative of the continuous wavelet transform, one or more gait features.

28. In an embodiment, the method of any of embodiments 25-27 is disclosed, wherein the one or more gait features comprise step duration, stride duration, step frequency, heel-strike events, toe-off events, stance-phase parameters (e.g. duration, average duration, frequency, average frequency, . . . ), swing-phase parameters (e.g. duration, average duration, frequency, average frequency, . . . ), indirect gait features, wherein indirect gait features can comprise the subject's cadence, fatigue, stability, rhythm/variability, asymmetry, pace, forward balance, lateral balance.

29. In an embodiment, the method of the preceding embodiment is disclosed, further comprising extracting one or more summarized gait features over the one or more signal blocks.

30. In an embodiment, the method of the preceding embodiment is disclosed, wherein the one or more summarized gait features comprise summarized metrics of the one or more gait features extracted for each of the one or more signal blocks.

31. In an embodiment, the method of the preceding embodiment is disclosed, wherein the summarized metrics comprise mean, median, trimmed versions thereof.

32. In an embodiment, the method of any of embodiments 25-31 is disclosed, wherein the step of calculating, using the determined directional components of the signal block, a step frequency comprises the steps of:
a. computing a first autocorrelation of the antero-posterior component of the signal block;
b. computing a second autocorrelation of the antero-posterior component of the signal block, wherein the second autocorrelation consists of an autocorrelation of the first autocorrelation of the antero-posterior component obtained in step a.;
c. computing a first autocorrelation of the vertical component of the signal block;
d. computing a second autocorrelation of the vertical component of the signal block, wherein the second autocorrelation consists of an autocorrelation of the first autocorrelation of the vertical component obtained in step c.;
e. computing a cross-correlation of the second autocorrelation of the antero-posterior component and of the second autocorrelation of the vertical component;
f. estimating the distance between peaks of the computed cross-correlation;
g. calculating, using the estimated distance, the step frequency.

33. In an embodiment, the method of any embodiments 25-31 is disclosed, wherein the step of calculating, using the determined directional components of the signal block, a step frequency comprises the steps of:
a. computing a first autocorrelation of the vertical component of the signal block;
b. computing a second autocorrelation of the vertical component of the signal block, wherein the second autocorrelation consists of an autocorrelation of the first autocorrelation of the vertical component obtained in step a.;
c. computing a first autocorrelation of the antero-posterior component of the signal block;
d. computing a second autocorrelation of the antero-posterior component of the signal block, wherein the second autocorrelation consists of an autocorrelation of the first autocorrelation of the antero-posterior component obtained in step c.;
e. computing a cross-correlation of the second autocorrelation of the antero-posterior component and of the second autocorrelation of the vertical component;
f. estimating the distance between peaks of the computed cross-correlation;
g. calculating, using the estimated distance, the step frequency.

34. In an embodiment, the method of any embodiments 25-33 is disclosed, wherein selecting one of the determined directional components of the signal block using the calculated step frequency and the computed autocorrelations of each directional component comprises the steps of:
a. calculating a power spectral density for each autocorrelation of each directional component;
b. selecting an interval comprising the calculated step frequency;
c. selecting the directional component with the highest power spectral density in the selected interval.

35. In an embodiment, the method of any embodiments 25-34 is disclosed, wherein obtaining a continuous wavelet transform of the selected directional component comprises obtaining a parameterized continuous wavelet function, and wherein obtaining the parameterized continuous wavelet function comprises estimating at least a wavelet scale and/or a wavelet sign.

36. In an embodiment, the method of any embodiments 25-34 is disclosed, wherein obtaining a continuous wavelet transform of the selected directional component comprises obtaining a parameterized continuous wavelet function.

37. In an embodiment, the method of any embodiments 25-34 is disclosed, wherein obtaining a continuous wavelet transform of the selected directional component comprises obtaining a parameterized continuous wavelet function, and wherein obtaining the parameterized continuous wavelet function comprises estimating at least a wavelet scale or a wavelet sign.

38. In an embodiment, the method of any embodiments 25-37 is disclosed, wherein the wavelet scale is a function of the calculated step frequency.
39. In an embodiment, the method of any embodiments 25-38 is disclosed, wherein estimating the wavelet sign comprises the steps of:
   a. computing a norm of the accelerometer signal of the signal block;
   b. computing a correlation of the parameterized continuous wavelet function and of the computed norm;
   c. determining, based on the sign of the computed correlation, the wavelet sign.
40. In an embodiment, a method of diagnosing or monitoring a neurological dysfunction associated with gait activity in a subject is disclosed, the method comprising analyzing the gait activity of the subject using the method of any preceding embodiment.
41. In an embodiment, a method of diagnosing a neurological dysfunction associated with gait activity in a subject is disclosed, the method comprising analyzing the gait activity of the subject using the method of any preceding embodiment.
42. In an embodiment, a method of monitoring a neurological dysfunction associated with gait activity in a subject is disclosed, the method comprising analyzing the gait activity of the subject using the method of any preceding embodiment.
43. In an embodiment, a method of diagnosing and monitoring a neurological dysfunction associated with gait activity in a subject is disclosed, the method comprising analyzing the gait activity of the subject using the method of any preceding embodiment.
44. In an embodiment, the method of any embodiments 40-43 is disclosed, wherein the neurological dysfunction is selected from: multiple sclerosis (MS), Parkinson's disease, Huntington's disease, optionally wherein the neurological dysfunction is MS.
45. In an embodiment, the method of any embodiments 40-43 is disclosed, wherein the neurological dysfunction is selected from: multiple sclerosis (MS), Parkinson's disease, Huntington's disease.
46. In an embodiment, the method of any embodiments 40-43 is disclosed, wherein the neurological dysfunction is MS.
47. In an embodiment, a system is disclosed, the system comprising:
   a. a processor; and
   b. a computer readable medium comprising instructions that, when executed by the processor, cause the processor to perform the steps of the method of any preceding embodiments.
48. In an embodiment, a system is disclosed, the system comprising:
   a. a processor; and
   b. a computer readable medium comprising instructions that, when executed by the processor, cause the processor to perform the steps of the method of any preceding embodiments; and
   c. optionally signal acquisition means, in particular one or more wearable motion sensors.
49. In an embodiment, a computer readable medium is disclosed comprising instructions which, when executed by a computer, cause the computer to perform the steps of the method of any preceding embodiments.
50. In an embodiment, a computer program [product] is disclosed comprising instructions which, when the program is executed by a computer, cause the computer to perform the steps of the method of any preceding embodiments.
51. Other embodiments of the present disclosure as hereinbefore described.

REFERENCES

All references cited herein are incorporated herein by reference in their entirety and for all purposes to the same extent as if each individual publication or patent or patent application was specifically and individually indicated to be incorporated by reference in its entirety.

Palmerini et al (2017), Identification of Characteristic Motor Patterns Preceding Freezing of Gait in Parkinson's Disease Using Wearable Sensors, Front. Neurol. 8:384.
Moe-Nilssen et al (2004), Estimation of gait cycle characteristics by trunk accelerometry, Journal of Biomechanics, Vol 37, Issue 1, January 2004, Pages 121-126.
McCamley et al (2012), An enhanced estimate of initial contact and final contact instants of time using lower trunk inertial sensor data, Gait Posture, June; 36(2): 316-8.
Godfrey et al (2014), The association between retirement and age on physical activity in older adults, Age Ageing, May; 43(3):386-93.
Del Din et al (2015), Validation of an accelerometer to quantify a comprehensive battery of gait characteristics in healthy older adults and Parkinson's disease: toward clinical and at home use, IEEE J. Biomed. Health Inform. 20, 838-47.
1820 Ning et al (2019), Appropriate mother wavelets for continuous gait event detection based on time-frequency analysis for hemiplegic and healthy individuals, Sensors (Basel), August 8; 19(16): 3462.
Zhou et al (2016), Towards real-time detection of gait events on different terrains using time-frequency analysis and peak heuristics algorithm, Sensors, 16, 1634.
1825 Pham et al (2017), Validation of a step detection algorithm during straight walking and turning in patients with Parkinson's disease and older adults using an inertial measurement unit at the lower back, Front. Neurol., Vol 8.
Caramia et al (2019), Optimizing the scale of a wavelet-based method for the detection of gait events from a waist-mounted accelerometer under different walking speeds, Sensors (Basel), April 19; 19(8):1869.
Angelini et al (2021), A multifactorial model of Multiple Sclerosis gait and its changes across different disability levels, IEEE Trans Biomed Eng, November 21; 68(11)": 3196-3204.

The invention claimed is:
1. A system, comprising:
at least one data processor; and
at least one memory storing instructions, which when executed by the at least one data processor, result in operations comprising:
   receiving, from one or more sensors configured to be located on a subject, a signal representative of a gait activity of the subject;
   identifying one or more directional components of the signal, the one or more directional components including a medio-lateral component and an antero-posterior component, and the one or more directional components being independent of an orientation of the one or more sensors on the subject;

validating, based at least on a medio-lateral autocorrelation of the medio-lateral component and an antero-posterior autocorrelation of the antero-posterior component, the medio-lateral component and the antero-posterior component;

in response to a failure to validate the medio-lateral component and the antero-posterior component, swapping the medio-lateral component and the antero-posterior component;

extracting, based at least on the one or more directional components of the signal, one or more gait features from the signal; and determining, based at least on the one or more gait features, at least one of a diagnosis, a progression, a treatment, and a treatment response for a neurological dysfunction.

2. The system of claim 1, wherein the extracting the one or more gait features includes calculating, based at least on the one or more directional components of the signal, a step frequency, determining, based at least on the step frequency, a wavelet transform of the one or more directional components; and determining, based at least on the wavelet transform, the one or more gait features.

3. The system of claim 2, wherein the calculating the step frequency includes determining a first vertical autocorrelation of a vertical component of the signal and a second vertical autocorrelation of the first vertical autocorrelation, determining a first antero-posterior autocorrelation of the antero-posterior component of the signal and a second antero-posterior autocorrelation of the first antero-posterior autocorrelation, determining a cross-correlation of the second vertical autocorrelation and the second antero-posterior autocorrelation, and determining, based at least on a distance between two or more peaks in the cross-correlation, the step frequency.

4. The system of claim 2, wherein the determining the wavelet transform includes convoluting, at successive timepoints, a wavelet across one directional component of the one or more directional components of the signal having a higher power in a frequency interval of the step frequency than other directional components of the one or more directional components of the signal.

5. The system of claim 4, wherein the determining the wavelet transform further includes calculating, for each directional component of the one or more directional components of the signal, a power density spectrum, selecting, as the frequency interval, a range of frequencies within a threshold of the step frequency, and identifying, based at least on the power density spectrum of each directional component of the one or more directional components of the signal, the one directional component of the signal having the higher power in the frequency interval of the step frequency than the other directional components of the one or more directional components of the signal.

6. The system of claim 2, wherein the operations further comprise:

determining, based at least on the wavelet transform, one or more of a toe-off event and a heel-strike event; and determining, based at least on the one or more of the toe-off event and the heel-strike event, the one or more gait features.

7. The system of claim 6, wherein the one or more gait features are determined based at least on a timing and/or a location of the one or more of the toe-off event and the heel-strike event.

8. The system of claim 6, wherein the heel-strike event is determined as a minimum of a first derivative of the wavelet transform.

9. The system of claim 6, wherein the toe-off event is determined as a maximum of a second derivative of the wavelet transform.

10. The system of claim 6, wherein the one or more gait features include at least one of cadence, fatigue, stability, rhythm, variability, asymmetry, pace, forward balance, and lateral balance.

11. The system of claim 1, wherein the operations further comprise:

dividing the signal into one or more signal blocks; and identifying, for each signal block, a vertical component, the antero-posterior component, and the medio-lateral component of the signal in the signal block.

12. The method of claim 1, wherein the operations further comprise:

determining the medio-lateral autocorrelation of the medio-lateral component and the antero-posterior autocorrelation of the antero-posterior component.

13. The system of claim 1, wherein the validating the medio-lateral component and the antero-posterior component identified for each signal block further includes validating the medio-lateral component and the antero-posterior component of the each signal block as correctly identified based at least on (i) the antero-posterior autocorrelation showing a first positive peak while the medio-lateral autocorrelation is showing a first negative peak, or (ii) a first peak of the antero-posterior autocorrelation having a highest absolute value where the first peak the antero-posterior autocorrelation and that of the medio-lateral autocorrelation are negative.

14. The system of claim 1, wherein the operations further comprise:

classifying each signal block as a rest block or a non-rest block; and identifying the one or more directional components of the signal in one or more non-rest blocks and not one or more rest blocks.

15. The system of claim 14, wherein the classifying each signal block as a rest block or a non-rest block includes classifying, based at least on a magnitude of an accelerometer signal and/or a gyroscope signal in a signal block, the signal block as a rest block or a non-rest block.

16. The system of claim 14, wherein the operations further comprise:

classifying, based at least on a presence of motion of a threshold magnitude in a single direction of movement or multiple directions of movement, each non-rest block as a straight-gait block or a non-straight gait block; and identifying the one or more directional components of the signal in one or more straight gait blocks and not one or more non-straight gait blocks.

17. The system of claim 1, wherein the operations further comprise:
applying one or more of an orientation filter, a statistical analysis, and a sensor fusion to identify the one or more directional components of the signal.

18. A computer-implemented method, comprising:
receiving, by one or more processors, a signal from one or more sensors configured to be located on a subject, the signal representative of a gait activity of the subject;
identifying, by the one or more processors, one or more directional components of the signal, the one or more directional components including a medio-lateral component and an antero-posterior component, and the one or more directional components being independent of an orientation of the one or more sensors on the subject;
validating, based at least on a medio-lateral autocorrelation of the medio-lateral component and an antero-posterior autocorrelation of the antero-posterior component, the medio-lateral component and the antero-posterior component;
in response to a failure to validate the medio-lateral component and the antero-posterior component, swapping the medio-lateral component and the antero-posterior component; extracting, by the one or more processors and based on at least on the one or more directional components of the signal, one or more gait features from the signal; and
determining, by the one or more processors and based at least on the one or more gait features, at least one of a diagnosis, a progression, a treatment, and a treatment response for a neurological dysfunction.

19. A non-transitory computer readable medium storing instructions, which when executed by at least one data processor, result in operations comprising:
receiving, from one or more sensors configured to be located on a subject, a signal representative of a gait activity of the subject;
identifying one or more directional components of the signal, the one or more directional components including a medio-lateral component and an antero-posterior component, and the one or more directional components being independent of an orientation of the one or more sensors on the subject;
validating, based at least on a medio-lateral autocorrelation of the medio-lateral component and an antero-posterior autocorrelation of the antero-posterior component, the medio-lateral component and the antero-posterior component; in response to a failure to validate the medio-lateral component and the antero-posterior component, swapping the medio-lateral component and the antero-posterior component;
extracting, based at least on the one or more directional components of the signal, one or more gait features from the signal; and
determining, based at least on the one or more gait features, at least one of a diagnosis, a progression, a treatment, and a treatment response for a neurological dysfunction.

\* \* \* \* \*